(12) United States Patent
Rieder et al.

(10) Patent No.: US 7,284,449 B2
(45) Date of Patent: Oct. 23, 2007

(54) IN-LINE MEASURING DEVICE

(75) Inventors: Alfred Rieder, Landshut (DE); Wolfgang Drahm, Freising (DE); Michael Fuchs, Eschbach (DE); Hans-Jörg Sprich, Schopfheim (DE); Ibho Itin, Liestal (CH); Samuel Wyss, Basel (CH)

(73) Assignee: Endress + Hauser Flowtec AG, Reinach (CH)

( * ) Notice: Subject to any disclaimer, the term of this patent is extended or adjusted under 35 U.S.C. 154(b) by 69 days.

(21) Appl. No.: 11/084,527

(22) Filed: Mar. 21, 2005

(65) Prior Publication Data

US 2006/0086196 A1    Apr. 27, 2006

Related U.S. Application Data

(60) Provisional application No. 60/570,490, filed on May 13, 2004, provisional application No. 60/556,491, filed on Mar. 26, 2004.

(30) Foreign Application Priority Data

Mar. 19, 2004  (DE) ...................... 10 2004 014 029
Apr. 30, 2004  (DE) ...................... 10 2004 021 690

(51) Int. Cl.
*G01F 1/84*  (2006.01)
(52) U.S. Cl. ................................. 73/861.356
(58) Field of Classification Search ........... 73/861.356, 73/861.355, 861.357, 152.47, 54.25
See application file for complete search history.

(56) References Cited

U.S. PATENT DOCUMENTS 4,187,721 A * 2/1980 Smith .................... 73/861.356

(Continued)

FOREIGN PATENT DOCUMENTS

EP    0 553 939 A2    8/1993

(Continued)

*Primary Examiner*—Jewel Thompson
(74) *Attorney, Agent, or Firm*—Bacon & Thomas

(57) ABSTRACT

An inline measuring device includes a vibration-type measurement pickup having at least one measuring tube, which has a medium to be measured flowing through it during operation. The measuring tube is made by means of an exciter arrangement to execute, at least at times and/or at least in part, lateral oscillations and, at least at times and/or at least in part, torsional oscillations about an imaginary measuring tube longitudinal axis. The torsional oscillations alternate with the lateral oscillations or are, at times, superimposed thereon. Also included is a sensor arrangement for producing oscillation measurement signals correspondingly representing oscillations of the measuring tube. Measuring device electronics controlling the exciter arrangement generates, by means of at least one of the oscillation measurement signals and/or by means of the exciter current, at least at times, at least one measured value, which represents the at least one physical quantity to be measured. Additionally, the measuring device electronics also determines a first intermediate value, which corresponds to the lateral current component of the exciter current serving to maintain the lateral oscillations of the measuring tube and/or to a damping of the lateral oscillations of the measuring tube, as well as a second intermediate value, which corresponds to a torsional current component of the exciter current serving to maintain the torsional oscillations of the measuring tube and/or to a damping of the torsional oscillations of the measuring tube. With the goal of producing the measured value at high accuracy, such value is determined also taking into consideration these two intermediate values. The measured value obtained in this way is distinguished especially by high accuracy also in the case of media of two, or more, phases.

15 Claims, 7 Drawing Sheets

U.S. PATENT DOCUMENTS

| | | | |
|---|---|---|---|
| 4,491,025 A * | 1/1985 | Smith et al. | 73/861.355 |
| 4,524,610 A * | 6/1985 | Fitzgerald et al. | 73/54.25 |
| 4,660,421 A | 4/1987 | Dahlin | |
| 4,733,569 A | 3/1988 | Kelsey | |
| 4,801,897 A * | 1/1989 | Flecken | 331/65 |
| 4,876,898 A | 10/1989 | Cage | |
| 5,069,074 A | 12/1991 | Young | |
| 5,218,873 A | 6/1993 | Lang | |
| 5,253,533 A | 10/1993 | Lam | |
| 5,301,557 A | 4/1994 | Cage | |
| 5,448,921 A | 9/1995 | Cage et al. | |
| 5,531,126 A | 7/1996 | Drahm | |
| 5,602,345 A | 2/1997 | Wenger | |
| 5,602,346 A | 2/1997 | Kitami | |
| 5,616,868 A | 4/1997 | Hagenmeyer | |
| 5,629,790 A * | 5/1997 | Neukermans et al. | 359/198 |
| 5,796,011 A | 8/1998 | Keita | |
| 5,869,770 A | 2/1999 | Yoshimura | |
| 6,006,609 A | 12/1999 | Drahm | |
| 6,378,364 B1 * | 4/2002 | Pelletier et al. | 73/152.47 |
| 6,505,519 B2 * | 1/2003 | Henry et al. | 73/861.356 |
| 6,513,393 B1 | 2/2003 | Eckert et al. | |
| 6,651,513 B2 | 11/2003 | Wenger | |
| 6,691,583 B2 | 2/2004 | Rieder | |
| 2001/0039839 A1 | 11/2001 | Ochiai | |
| 2002/0184940 A1 | 12/2002 | Storm | |
| 2003/0056574 A1 | 3/2003 | Drahm | |
| 2003/0208325 A1 | 11/2003 | Keilty | |
| 2003/0233878 A1 | 12/2003 | Drahm et al. | |
| 2004/0221660 A1 | 11/2004 | Dutton | |
| 2005/0022611 A1 | 2/2005 | Hemp | |
| 2005/0081643 A1 | 4/2005 | Mattar | |

FOREIGN PATENT DOCUMENTS

| | | |
|---|---|---|
| EP | 1 001 254 A1 | 5/2000 |
| EP | 1055102 B1 | 11/2000 |
| EP | 1154254 A1 | 11/2001 |
| EP | 1158289 A1 | 11/2001 |
| EP | 1 281 938 A2 | 2/2003 |
| EP | 1281938 A3 | 2/2003 |
| EP | 1 291 639 A1 | 3/2003 |
| WO | WO 88/03261 | 5/1988 |
| WO | WO 95/16897 | 6/1995 |
| WO | WO 98/07009 | 2/1998 |
| WO | WO 99/39164 | 8/1999 |
| WO | WO 00/57141 | 9/2000 |
| WO | WO 01/33174 A1 | 5/2001 |
| WO | WO 02/37063 A2 | 5/2002 |
| WO | WO 03/076880 A1 | 9/2003 |
| WO | WO 03/095949 A1 | 11/2003 |
| WO | WO 03/095950 A1 | 11/2003 |

* cited by examiner

IN-LINE MEASURING DEVICE

FIELD OF THE INVENTION

The invention relates to an inline measuring device having a vibratory-type measurement pickup, especially a Coriolis mass-flow/density measuring device for a medium, especially a two, or more, phase medium flowing in a pipeline, as well as a method for producing by means of such a measurement pickup a measured value representing a physical, measured quantity of the medium, for example a mass flow rate, a density and/or a viscosity.

BACKGROUND OF THE INVENTION

In the technology of process measurements and automation, the measurement of physical parameters of a medium flowing in a pipeline, parameters such as e.g. the mass flow rate, density and/or viscosity, such inline measuring devices, especially Coriolis mass flow measuring devices, are used, which bring about reaction forces in the medium, such as e.g. Coriolis forces corresponding to the mass flow rate, inertial forces corresponding to the density, or frictional forces corresponding to the viscosity, etc., by means of a vibratory measurement pickup inserted into the course of the pipeline carrying the medium and traversed during operation by the medium, and by means of a measurement and operating circuit connected therewith. Derived from these reaction forces, the measuring devices then produce a measurement signal representing the particular mass flow rate, the particular viscosity and/or the particular density of the medium.

Inline measuring devices of this type, utilizing a vibratory measurement pickup, as well as their manner of operation, are known per se to those skilled in the art and are described in detail in e.g. WO-A 03/095950, WO-A 03/095949, WO-A 03/076880, WO-A 02/37063, WO-A 01/33174, WO-A 00/57141, WO-A 99/39164, WO-A 98/07009, WO-A 95/16897, WO-A 88/03261, U.S. 2003/0208325, U.S. Pat. No. 6,691,583, U.S. Pat. No. 66 51 51 13, U.S. Pat. No. 6,513,393, U.S. Pat. No. 6,505,519, U.S. Pat. No. 6,006,609, U.S. Pat. No. 5,869,770, U.S. Pat. No. 5,796,011, U.S. Pat. No. 5,616,868, U.S. Pat. No. 5,602,346, U.S. Pat. No. 5,602,345, U.S. Pat. No. 5,531,126, U.S. Pat. No. 5,301,557, U.S. Pat. No. 5,253,533, U.S. Pat. No. 5,218,873, U.S. Pat. No. 5,069,074, U.S. Pat. No. 4,876,898, U.S. Pat. No. 4,733,569, U.S. Pat. No. 4,660,421, U.S. Pat. No. 4,524,610, U.S. Pat. No. 4,491,025, U.S. Pat. No. 4,187,721, EP-A 1 291 639, EP-A 1 281 938, EP-A 1 001 254 or EP-A 553 939.

For guiding the medium, the measurement pickups include at least one measuring tube with a straight tube segment held in a, for example, tubular or box-shaped, support frame. For producing the above-mentioned reaction forces during operation, the tube segment is caused to vibrate, driven by an electromechanical exciter arrangement. For registering vibrations of the tube segment, particularly at its inlet and outlet ends, the measurement pickups additionally include an electrophysical sensor arrangement reacting to movements of the tube segment.

In the case of Coriolis mass flow measuring devices, the measurement of the mass flow rate of a medium flowing in a pipeline rests, for example, on having the medium flow through the measuring tube inserted into the pipeline and oscillating during operation laterally to a measuring tube axis, whereby Coriolis forces are induced in the medium. These, in turn, effect that the inlet and outlet end regions of the measuring tube oscillate shifted in phase relative to one another. The magnitude of this phase shift serves as a measure of the mass flow rate. The oscillations of the measuring tube are, to this end, registered by means of two oscillation sensors of the above-mentioned sensor arrangement separated from one another along the length of the measuring tube and are transformed into oscillation measurement signals, from whose phase shift relative to one another the mass flow rate is derived.

Already the above-mentioned U.S. Pat. No. 4,187,721 mentions, further, that the instantaneous density of the flowing medium can also be measured by means of such inline measuring devices, and, indeed, on the basis of a frequency of at least one of the oscillation measurement signals delivered from the sensor arrangement. Moreover, usually also a temperature of the medium is directly measured in suitable manner, for example by means of a temperature sensor arranged on the measuring tube. Additionally, straight measuring tubes can, as is known, upon being excited to torsional oscillations about a torsional oscillation axis extending essentially parallel to, or coinciding with, the longitudinal axis of the measuring tube, effect that radial shearing forces are produced in the medium as it flows through the tube, whereby significant oscillation energy is withdrawn from the torsional oscillations and dissipated in the medium. As a result of this, a considerable damping of the torsional oscillations of the oscillating measuring tube occurs, so that, additionally, electrical exciting power must be added, in order to maintain the torsional oscillations. On the basis of the electrical exciting power required to maintain the torsional oscillations of the measuring tube, the measurement pickup can also be used to determine, at least approximately, a viscosity of the medium; compare, in this connection also U.S. Pat. No. 4,524,610, U.S. Pat. No. 5,253,533, U.S. Pat. No. 6,006,609 or U.S. Pat. No. 6,651,513. It can, consequently, assumed, without more in the following, that, even when not expressly stated, modern inline measuring devices using a vibratory measurement pickup, especially Coriolis mass flow measuring devices, have the ability to measure, in any case, also density, viscosity and/or temperature of the medium, especially since these are always needed anyway in the measurement of mass flow rate for the compensation of measurement errors arising from fluctuating density and/or viscosity of the medium; compare, in this connection, especially the already mentioned U.S. Pat. No. 6,513,393, U.S. Pat. No. 6,006,609, U.S. Pat. No. 5,602,346, WO-A 02/37063, WO-A 99/39164 or also WO-A 00/36379.

In the application of inline measuring devices using a vibratory measurement-pickup, it has, however, become evident, as also discussed, for example, in JP-A 10-281846, WO-A 03/076880, EP-A 1 291 639, U.S. Pat. No. 6,505,519 or U.S. Pat. No. 4,524,610, that, in the case of inhomogeneous media, especially two, or more, phase media, the oscillation measurement signals derived from the oscillations of the measuring tube, especially also the mentioned phase shift, can be subject to fluctuations to a considerable degree and, thus, in some cases, can be completely unusable for the measurement of the desired physical parameters, without the use of auxiliary measures, this in spite of keeping the viscosity and density in the individual phases of the medium, as well as also the mass flow rate, practically constant and/or appropriately taking them into consideration. Such inhomogeneous media can, for example, be liquids, into which, as is e.g. practically unavoidable in dosing or bottling processes, a gas, especially air, present in the pipeline is entrained or out of which a dissolved medium, e.g. carbon dioxide, outgasses and leads to foam formation.

As other examples of such inhomogeneous media, emulsions and wet, or saturated, steam can be named. As causes for the fluctuations arising in the measurement of inhomogeneous media by means of vibratory measurement pickups, the following can be noted by way of example: the unilateral clinging or deposit of gas bubbles or solid particles, entrained in liquids, internally on the measuring tube wall, and the so-called "bubble-effect", where gas bubbles entrained in the liquid act as flow bodies for liquid volumes accelerated transversely to the longitudinal axis of the measuring tube.

While, for decreasing the measurement errors associated with two, or more, phase media, a flow, respectively medium, conditioning preceding the actual flow rate measurement is proposed in WO-A 03/076880, both JP-A 10-281846 and U.S. Pat. No. 6,505,519, for example, describe a correction of the flow rate measurement, especially the mass flow rate measurement, based on the oscillation measurement signals, which correction rests especially on the evaluation of deficits between a highly accurately measured, actual medium density and an apparent medium density determined by means of Coriolis mass flow measuring devices during operation.

In particular, pre-trained, in some cases even adaptive, classifiers of the oscillation measurement signals are proposed for this. The classifiers can, for example, be designed as a Kohonen map or neural network, and the correction is made either on the basis of some few parameters, especially the mass flow rate and the density measured during operation, as well as other features derived therefrom, or also using an interval of the oscillation measurement signals encompassing one or more oscillation periods. The use of such a classifier brings, for example, the advantage that, in comparison to conventional Coriolis mass flow/density meters, no, or only very slight, changes have to be made at the measurement pickup, in terms of mechanical construction, the exciter arrangement or the operating circuit driving such, which are specially adapted for the particular application. However, a considerable disadvantage of such classifiers includes, among others, that, in comparison to conventional Coriolis mass flow measuring devices, considerable changes are required in the area of the measured value production, above all with regards to the analog-to-digital transducer being used and the microprocessors. As, namely, also described in U.S. Pat. No. 6,505,519, required for such a signal evaluation, for example, in the digitizing of the oscillation measurement signals, which can exhibit an oscillation frequency of about 80 Hz, is a sampling rate of about 55 kHz or more, in order to obtain a sufficient accuracy. Stated differently, the oscillation measurement signals have to be samples with a sampling ratio of far above 600:1. Beyond this, also the firmware stored and executed in the digital measurement circuit is correspondingly complex. A further disadvantage of such classifiers is that they must be trained and correspondingly validated for the conditions of measurement actually existing during operation of the measurement pickup, be it regarding the particulars of the installation, the medium to be measured and its usually variable properties, or other factors influencing the accuracy of measurement. Because of the high complexity of the interplay of all these factors, the training and its validation can occur ultimately only on site and individually for each measurement pickup, this in turn meaning a considerable effort for the startup of the measurement pickup. Finally, it has been found, that such classifier algorithms, on the one hand because of the high complexity, on the other because of the fact that usually a corresponding physical-mathematical model with technically relevant or comprehensible parameters is not explicitly present, exhibit a very low transparency and are, consequently, often difficult to explain. Accompanying this situation, it is clear that considerable reservations can occur on the part of the customer, with such acceptance problems especially arising when the classifier, additionally, is self-adapting, for example a neural network.

As a further possibility for getting around the problem of inhomogeneous media, it is proposed, for instance, already in U.S. Pat. No. 4,524,610 to install the measurement pickup such that the straight measuring tube extends essentially vertically, in order to prevent, as much as possible, a deposition of such disturbing, especially gaseous, inhomogeneities. Here, however, one is dealing with a very special solution which cannot always be implemented, without more, in the technology of industrial process measurement. On the one hand, in this case, it can happen, namely, that the pipeline, into which the measurement pickup is to be inserted, might have to be adapted to the measurement pickup, rather than the reverse, which can mean an increased expense for implementing the measurement location. On the other hand, as already mentioned, the measuring tubes might have a curved shape, in which case the problem cannot always be solved satisfactorily by an adapting of the installation orientation anyway. It has, moreover, been found in this case that the aforementioned corruptions of the measurement signal are not necessarily prevented with certainty by the use of a vertically installed, straight measuring tube anyway.

SUMMARY OF THE INVENTION

An object of the invention is, therefore, to provide a corresponding inline measuring device, especially a Coriolis mass flow measuring device, that is suited for measuring a physical, measured quantity, especially mass flow rate, density and/or viscosity, very accurately, even in the case of inhomogeneous, especially two, or more, phase media, and, indeed, especially desirably with a measurement error of less than 10% referenced to the actual value of the measured quantity. A further object is to provide a corresponding method for producing a corresponding measured value.

For achieving this object, the invention resides in an inline measuring device, especially a Coriolis mass flow rate/density measuring device and/or a viscosity measuring device, for measuring at least one physical, measured quantity, especially a mass flow rate, a density and/or a viscosity, of a medium, especially a two, or more, phase medium, conducted in a pipeline. The inline measuring device includes for this purpose a vibratory measurement pickup and a measuring device electronics electrically coupled with the measurement pickup. The measurement pickup includes, inserted into the course of the pipeline, a measuring tube, especially an essentially straight measuring tube, thus communicating with the pipeline and serving to conduct the medium to be measured, an exciter arrangement acting on the measuring tube for causing the at least one measuring tube to vibrate, and a sensor arrangement for registering vibrations of the at least one measuring tube and delivering at least one oscillation measurement signal representing oscillations of the measuring tube. The exciter arrangement causes the measuring tube, during operation, at least at times and/or at least partially, to vibrate with lateral oscillations, especially bending oscillations. Additionally, the exciter arrangement causes the measuring tube, during operation, at least at times and/or at least partially, to vibrate with torsional oscillations about an imaginary, measuring tube longitudinal axis essentially aligned with the measuring tube, especially an axis developed as a principal axis of inertia of the measuring tube. The torsional oscillations are especially ones which alternate with the lateral oscillations or are at times superimposed thereon. The measuring device electronics delivers, at least at times, an exciting current driving the exciter arrangement. Further, the measuring device electronics determines a first intermediate value, which corresponds to a lateral current component of the exciter current serving for maintaining the lateral oscillations of the measuring tube and/or to a damping of the lateral oscillations of the exciter current. Additionally, the measuring device electronics determines a second intermediate value, which corresponds to a torsional current component of the exciter current serving for maintaining the torsional oscillations of the measuring tube and/or to a damping of the torsional oscillations of the measuring tube. By means of the at least one oscillation measurement signal and/or by means of the exciter current, as well as with application of the first and second intermediate values, the measuring device electronics generates, at least at times, at least one measured value, which represents the at least one physical quantity being measured, especially the mass flow rate, the density or the viscosity of the medium.

Additionally, the invention resides in a method for measuring a physical, measured quantity, especially mass flow rate, a density and/or a viscosity, of a medium flowing in a pipeline, especially a two, or more, phase medium, by means of an inline measuring device having a vibratory measurement pickup, especially a Coriolis mass flow measuring device, and a measuring device electronics electrically coupled with the pickup, which method comprises the following steps:

allowing a medium to be measured to flow through at least one measuring tube of the measurement pickup communicating with the pipeline and feeding an exciter current into an exciter arrangement mechanically coupled with the measuring tube guiding the medium, in order to cause the measuring tube to execute mechanical oscillations, effecting lateral oscillations, especially bending oscillations, of the measuring tube and effecting torsional oscillations of the measuring tube, especially torsional oscillations superimposed on the lateral oscillations, registering vibrations of the measuring tube and producing at least one oscillation measurement signal representing oscillations of the measuring tube, determining a first intermediate value derived from the exciter current and corresponding to a lateral current component of the exciter current serving for maintaining the lateral oscillations of the measuring tube and/or to a damping of the lateral oscillations of the measuring tube, determining a second intermediate value derived from the exciter current and corresponding to a torsional current component of the exciter current serving for maintaining the torsional oscillations of the measuring tube and/or to a damping of the torsional oscillations of the measuring tube, and using the at least one oscillation measurement signal and/or the exciter current, as well as the first and second intermediate values, for producing a measured value representing the physical quantity to be measured.

According to a first embodiment of the inline measuring device of the invention, the measuring electronics determines, derived from the at least one oscillation measurement signal and/or from the exciter current, an initial measured value, which corresponds, at least approximately, to the at least one quantity to be measured, and, on the basis of the first and second intermediate values, a correction value for the initial measured value, and the measuring device electronics generates the measured value by means of the initial measured value and the correction value.

In a second embodiment of the inline measuring device of the invention, the measuring tube, driven by the exciter arrangement, executes torsional oscillations having a measuring tube torsional oscillation frequency which is set to be different from a measuring tube bending oscillation frequency with which the measuring tube, driven by the exciter arrangement, executes lateral oscillations.

According to a third embodiment of the inline measuring device of the invention, the measuring tube communicates with the connected pipeline via an inlet tube piece opening into an inlet end and via an outlet tube piece opening into an outlet end, and the measurement pickup includes a counteroscillator fixed to the inlet end and to the outlet end of the measuring tube, especially also mechanically coupled with the exciter arrangement, and vibrating, at least at times, during operation, especially with phase opposite to that of the measuring tube.

In a fourth embodiment of the inline measuring device of the invention, the measuring device electronics determines the correction value on the basis of a comparison of the first intermediate value with the second intermediate value and/or on the basis of a difference existing between the first intermediate value and the second intermediate value.

According to a fifth embodiment of the inline measuring device of the invention, the measuring device electronics produces the first and/or the second intermediate value also on the basis of the least one oscillation measurement signal.

In a sixth embodiment of the inline measuring device of the invention, the at least one measured value represents a viscosity of the medium flowing in the measuring tube, and the measuring device electronics determines also the initial measured value on the basis of the exciter current, and/or a component of the exciter current, driving the exciter arrangement.

According to a seventh embodiment of the inline measuring device of the invention, the at least one measured value represents a density of the medium flowing in the measuring tube, and the measuring tube electronics determines the initial measured value using the at least one oscillation measurement signal and/or the exciter current by recognizing that this corresponds to the density to be measured and/or to an oscillation frequency of the at least one oscillation measurement signal.

In an eighth embodiment of the inline measurement device of the invention, the measuring device electronics determines at least at times, on the basis of the first and second intermediate values, a concentration measured value, which represents an, especially relative, volume and/or mass fraction of a phase of the medium, in the case of a two, or more, phase medium in the measuring tube.

According to a ninth embodiment of the inline measuring device of the invention, the sensor arrangement delivers at least one oscillation measurement signal representing, at least in part, inlet end lateral oscillations, especially bending oscillations, of the measuring tube, and at least one second oscillation measurement signal representing, at least in part, outlet end lateral oscillations, especially bending oscillations, of the measuring tube.

In a tenth embodiment of the inline measuring device of the invention, the at least one measured value represents a mass flow rate of the medium flowing in the measuring tube, and the measuring device electronics determines the initial measured value using the two oscillation measurement signals by recognizing that this corresponds to the mass flow rate to be measured and/or to a phase difference between the two oscillation measurement signals.

According to a first embodiment of the method of the invention, the step of producing the measured value includes the steps of:

developing, using the at least one oscillation measurement signal and/or the exciter current, an initial measured value corresponding at least approximately to the physical quantity to be measured, producing a correction value for the initial value by means of the first and second intermediate values, and correcting the initial measured value by means of the correction value, for producing the measured value.

In a second embodiment of the method of the invention, the step of producing the correction value for the initial measurement value comprises the steps of:

Comparing the first intermediate value with the second intermediate value for determining a difference existing between the two intermediate values and determining, taking into consideration the difference existing between the two intermediate values, a concentration measured value, which represents, in the case of a two, or more, phase medium in the measuring tube, an, especially relative, volume and/or mass fraction of a medium phase.

A basic idea of the invention resides in operating the measurement pickup in a dual-mode for the purpose of correcting or compensating possible measurement errors caused especially by inhomogeneities in the medium to be measured. In the dual mode, the measuring tube is caused to vibrate alternately in at least two oscillation modes which are essentially independent of one another, namely a lateral oscillation mode and a torsional oscillation mode. On the basis of operating parameters of the measurement pickup determined during the dual-mode operation, especially the exciter current, the frequencies and/or amplitudes of the oscillations of the measuring tube, etc., required for maintaining the lateral and torsional oscillations of the measuring tube, very exact and amazingly robust correction values for the actual measured values can be determined in a very simple manner.

The invention rests, in this connection, especially on the discovery that the exciter power fed into the measurement pickup for maintaining the lateral oscillations of the measuring tube can be affected to a high degree by inhomogeneities in the medium being measured, inhomogeneities such as e.g. entrained gas bubbles or solid particles, etc. In comparison therewith, the exciter power fed into the measurement pickup for maintaining torsional oscillations of the measuring tube depend to a considerably lesser extent on such inhomogeneities, so that, during operation, based on this exciter power, especially based on the exciter current component actually fed for maintaining the torsional oscillations, up-to-the-moment reference values can be determined, with whose help a comparison of the correspondingly determined measured values for the lateral oscillations, for example the exciter current component actually fed for maintaining the lateral oscillations, can be made. On the basis of this, for example, normalized or subtractively executed comparison, an instantaneous degree of inhomogeneity in the medium can be estimated and, derived from this, a sufficiently accurate conclusion made as to the measurement error which has entered the measurement. The inline measuring device of the invention is, therefore, especially suited for the measurement of a physical, measured quantity, especially a mass flow rate, a density and/or a viscosity, even of a two, or more, phase medium flowing in a pipeline, especially a liquid-gas mixture.

An advantage of the invention is that the correction values to be determined are well reproducible over a large range of application and, also, the forming rules for determining the correction values during measurement operation can be formulated relatively simply.

Moreover, these forming rules can be calculated initially with a relatively small effort. A further advantage of the invention is, additionally, to be seen in the fact that, in the case of the inline measuring device of the invention, as compared to a conventional type, especially such as described in WO-A 03/095950, WO-A 03/095949 or U.S. Pat. No. 4,524,610, only in the case of the usually digital, measured value production do slight changes have to be made, these being essentially limited to the firmware, while, both in the case of the measurement pickup and in the production and preprocessing of the oscillation measurement signals, no, or only slight, changes are required. Thus, for example, even in the case of two, or more, media, the oscillation measurement signals can be sampled, as before, with a usual sampling ratio of far under 100:1, especially of about 10:1.

BRIEF DESCRIPTION OF THE DRAWINGS

The invention and further advantageous embodiments will now be explained in detail on the basis of examples of embodiments presented in the figures of the drawing. Equal parts are provided in all figures with equal reference characters; when required in the interest of clarity, already mentioned reference characters are omitted in subsequent figures.

DESCRIPTION OF THE PREFERRED EMBODIMENT

Figure 1:
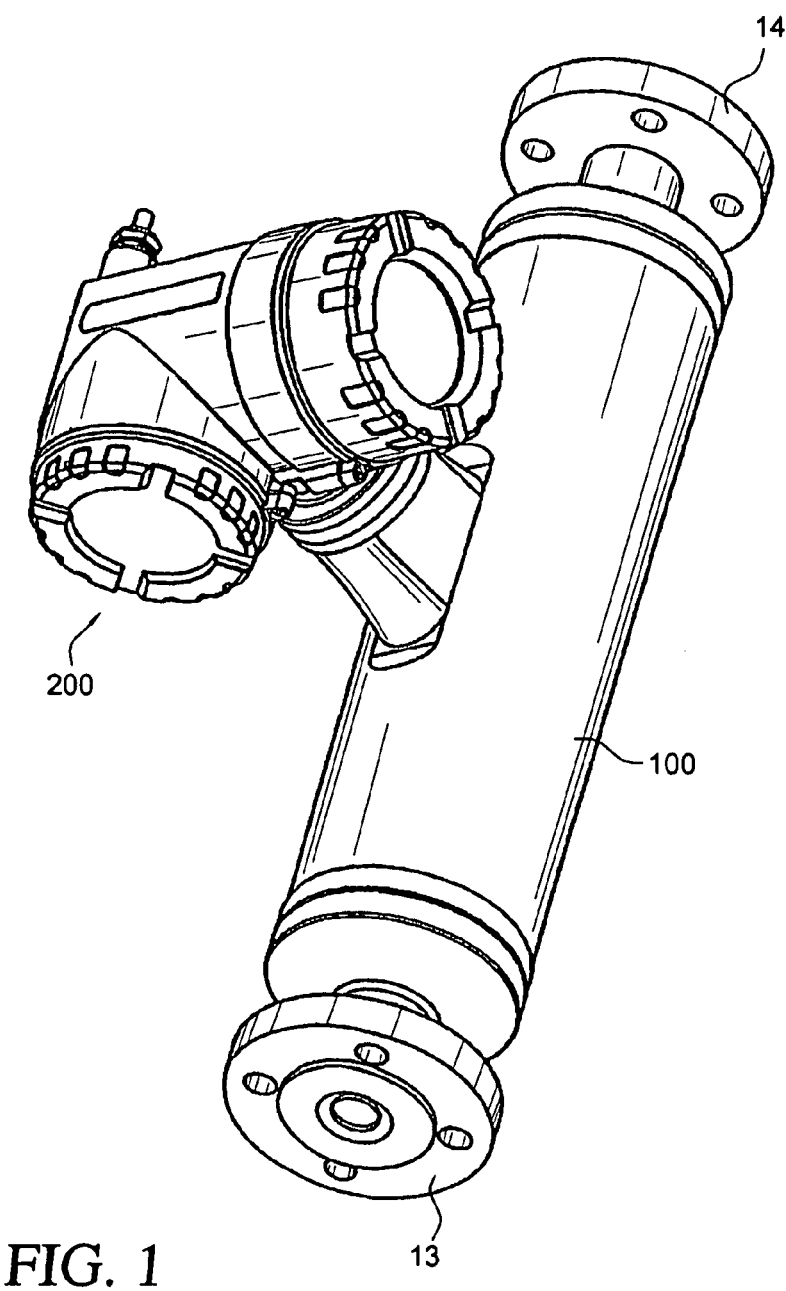
FIG. 1 shows an inline measuring device which can be inserted into a pipeline for measuring a mass flow rate of a fluid guided in the pipeline.

FIG. 1 shows, perspectively, an inline measuring device 1 suited for registering a physical, measured quantity, e.g. a mass flow rate m, a density $\rho$ and/or a viscosity $\eta$, of a medium flowing in a pipeline (not shown) and for imaging this measured quantity in an instantaneously representing, measured value $X_x$. The medium in this instance can be practically any flowable substance, for example a liquid, a gas, a vapor, or the like.

Figure 2:
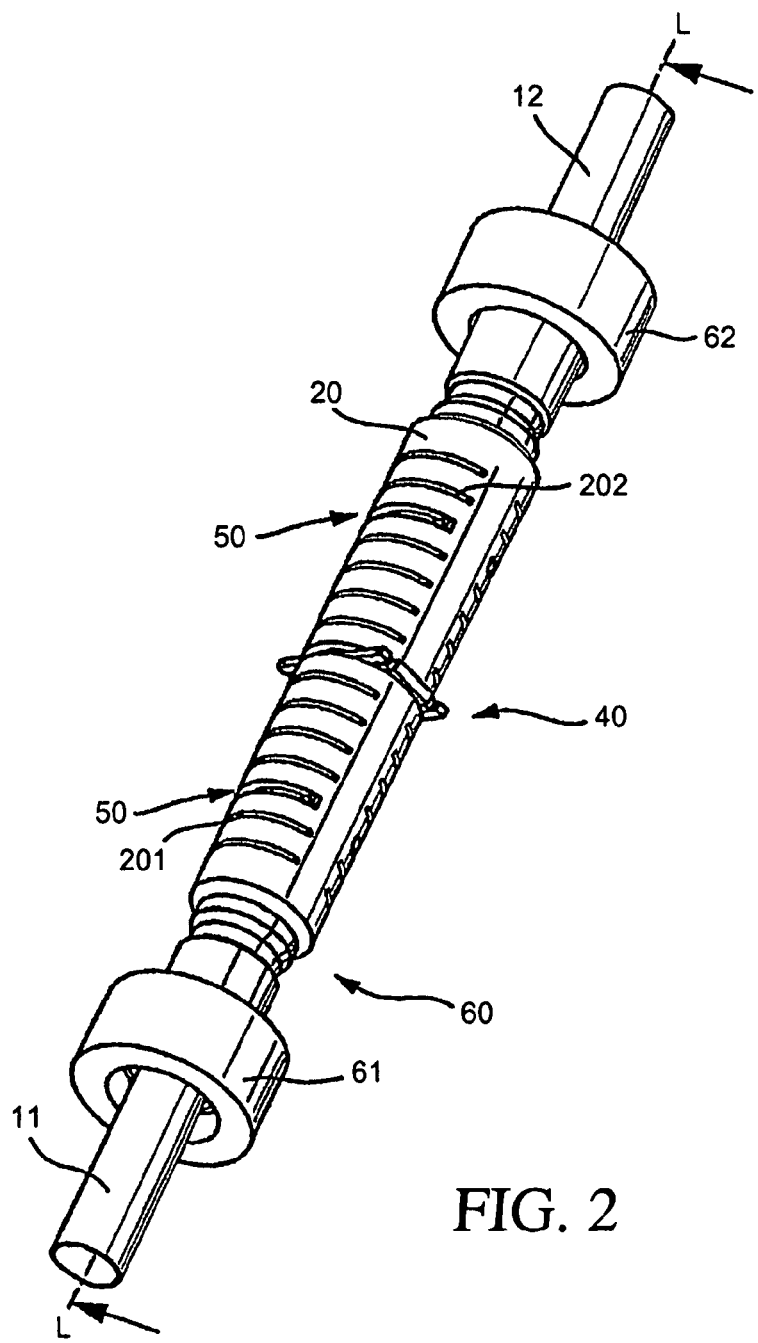
FIG. 2 shows, in a perspective, side view, an example of an embodiment for a measurement pickup suited for the measuring device of FIG. 1.
Figure 7:
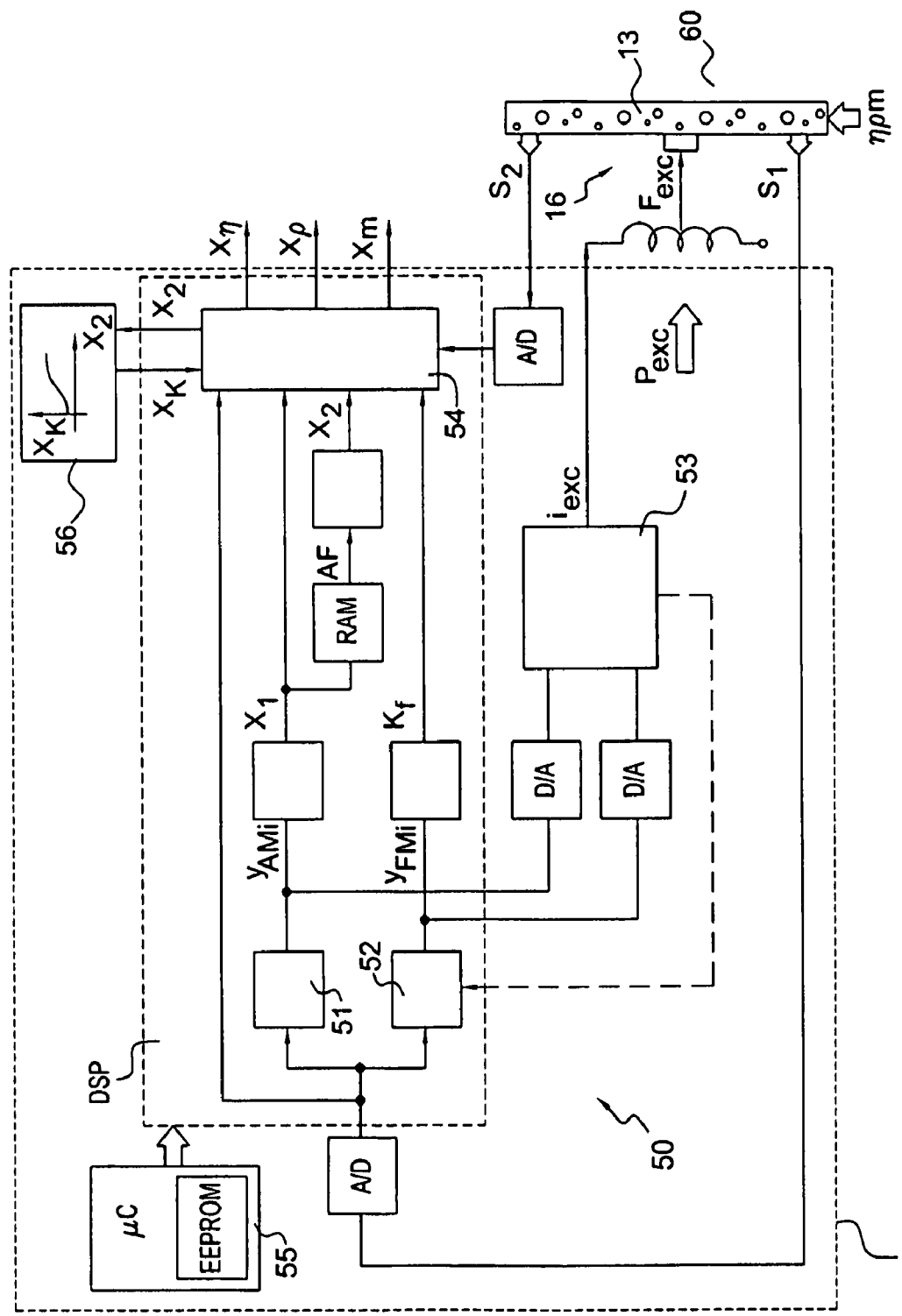
FIG. 7 shows schematically in the form of a block diagram a preferred embodiment of a measuring device electronics suited for the inline measuring device of FIG. 1, and FIGS. 8 and 9 show, graphically, measurement data experimentally determined using an inline measuring device of the FIGS. 1 to 7.

The inline measuring device 1, for example provided in the form of a Coriolis mass flow, density and/or viscosity meter, includes therefor a vibratory measurement pickup 10 flowed-through by the medium to be measured, an example of an embodiment and developments being shown in FIGS. 2 to 6, together with a measuring device electronics 50, as illustrated schematically in FIGS. 2 and 7. Preferably, the measuring device electronics 50 is, additionally, so designed that it can, during operation of the inline measuring device 1, exchange measurement and/or operational data with a measured value processing unit superordinated, i.e. located at a higher level, with respect thereto, for example a programmable logic controller (PLC), a personal computer and/or a workstation, via a data transmission system, for example a field bus system. Furthermore, the measuring device electronics is designed such that it can be supplied from an external energy supply, for example also over the aforementioned field bus system.

For the case in which the vibratory measuring device is provided for coupling to a field bus or some other communication system, the, especially programmable, measuring device electronics 50 is equipped with a corresponding communications interface for a communication of data, e.g. for the transmission of the measurement data to the already mentioned, programmable logic controller or to a superordinated process control system. For accommodation of the measuring device electronics 50, an electronics housing 200 is additionally provided, especially one mounted externally directly onto the measurement pickup 10, but even one possibly set apart from such.

Figure 3:
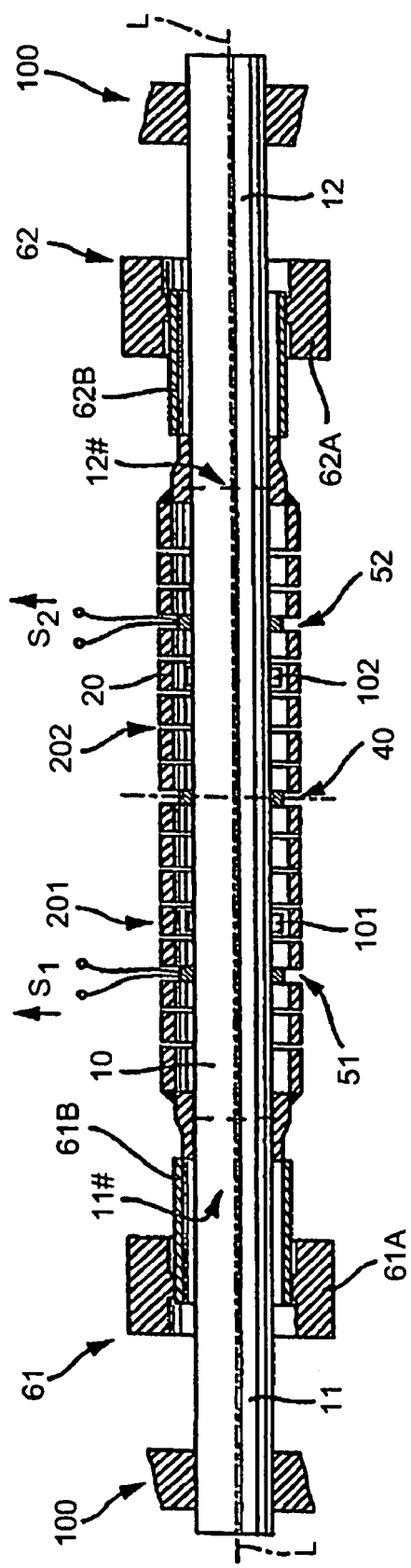
FIG. 3 shows, sectioned in a side view, the measurement pickup of FIG. 2.
Figure 4:
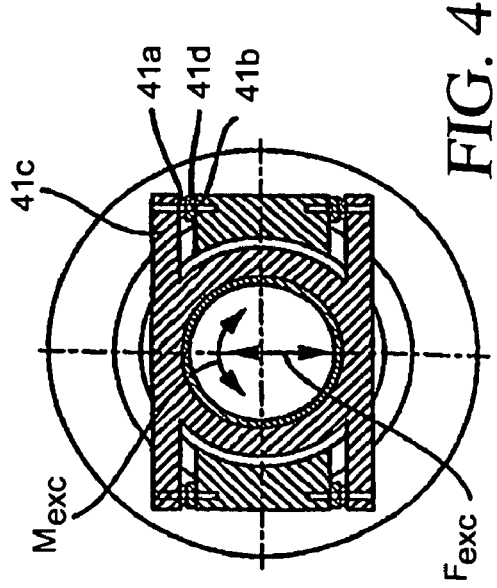
FIG. 4 shows the measurement pickup of FIG. 2 in a first cross section.
Figure 6:
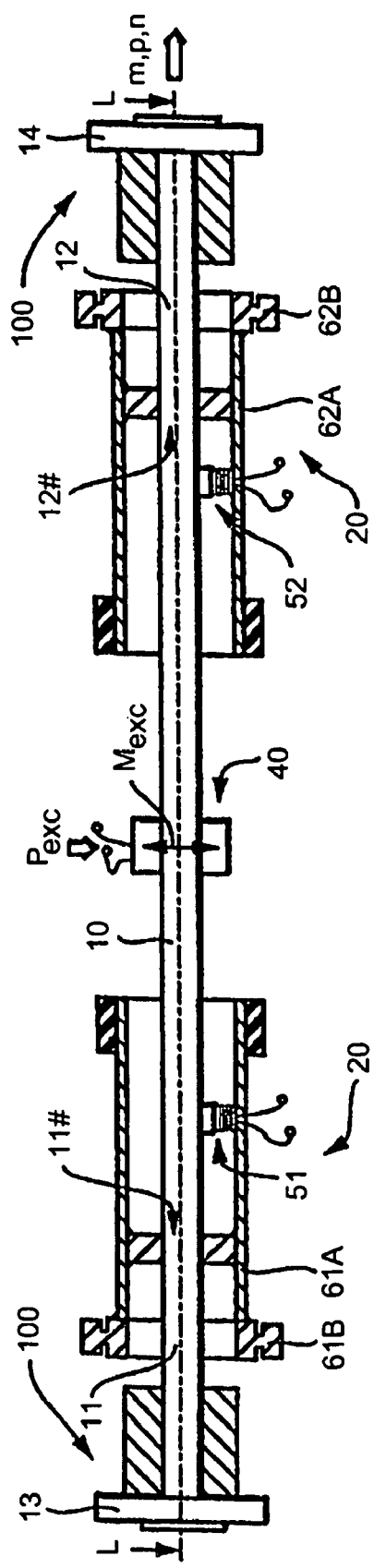
FIG. 6 shows, sectioned in a side view, a further example of an embodiment of a vibratory measurement-pickup suited for the inline measuring device of FIG. 1.

As already mentioned, the inline measuring device includes a vibratory measurement pickup, which is flowed-through by the medium to be measured, and which serves for producing, in a through-flowing medium, mechanical reaction forces, especially Coriolis forces, dependent on the mass flow rate, inertial forces dependent on the density of the medium and/or frictional forces dependent on the viscosity of the medium, forces which react measurably, i.e. capable of being detected by sensor, on the measurement pickup. Derived from these reaction forces characterizing the medium, e.g. the mass flow rate, the density and/or the viscosity of the medium can be measured in manner known to those skilled in the art. In FIGS. 3 and 4, an example of an embodiment of an electrophysical transducer arrangement, serving as a vibratory measurement pickup 10, is schematically illustrated. The mechanical construction and manner of functioning of such a transducer arrangement is known per se to those skilled in the art and is also described in detail in U.S. Pat. No. 6,691,583, WO-A 03/095949 or WO-A 03/095950.

For guiding the medium and for producing said reaction forces, the measurement pickup includes at least one, essentially straight, measuring tube 10 of predeterminable measuring tube diameter.

Measuring tube 10 is caused, during operation, to vibrate, at least at times, and is repeatedly elastically deformed thereby.

Elastic deformation of the measuring tube lumen means here, that a spatial form and/or a spatial position of the measuring tube lumen is changed within an elastic range of the measuring tube 10 in predeterminable manner cyclically, especially periodically; compare, in this connection, also U.S. Pat. No. 4,801,897, U.S. Pat. No. 5,648,616, U.S. Pat. No. 5,796,011, U.S. Pat. No. 6,006,609, U.S. Pat. No. 6,691,583, WO-A 03/095949 and/or WO-A 03/095950. It should be mentioned here that, instead of the measurement pickup shown in the example of an embodiment having a single, straight measuring tube, the measurement pickup serving for implementation of the invention can, as well, be selected from a multiplicity of vibratory measurement pickups known in the state of the art. In particular, suited, for example, are vibratory measurement pickups having two parallel, straight measuring tubes flowed-through by the medium to be measured, such as are described in detail also in U.S. Pat. No. 5,602,345.

As shown in FIG. 1, the measurement pickup 1 additionally has a measurement pickup housing 100 surrounding the measuring tube 10, as well as surrounding possible other components of the measurement pickup (see also further below). Housing 100 acts to protect tube 10 and other components from damaging environmental influences and/or to damp possible outwardly-directed sound emissions of the measurement pickup. Beyond this, the measurement pickup housing 100 also serves as a mounting platform for an electronics housing 200 housing the measuring device electronics 50. To this end, the measurement pickup housing 100 is provided with a neck-like transition piece, on which the electronics housing 200 is appropriately fixed; compare FIG. 1. Instead of the tube-shaped transducer housing 100 shown here extending coaxially with the measuring tube, other suitable housing forms can, of course, be used, such as e.g. box-shaped structures.

The measuring tube 10, which communicates in the usual manner at inlet and outlet ends with the pipeline introducing, respectively extracting, the medium to be measured, is oscillatably suspended in the preferably rigid, especially bending- and twisting-stiff, transducer housing 100. For permitting the medium to flow through, the measuring tube is connected to the pipeline via an inlet tube piece 11 opening into the inlet end 11# and an outlet tube piece 12 opening into the outlet end 12#. Measuring tube 10, inlet tube piece 11 and outlet tube piece 12 are aligned with one another and with the above-mentioned measuring tube longitudinal axis L as exactly as possible and are, advantageously, provided as one piece, so that e.g. a single, tubular stock can serve for their manufacture; in case required, measuring tube 10 and tube pieces 11, 12 can, however, also be manufactured by means of separate, subsequently joined, e.g. welded, stock. For manufacture of the measuring tube 10, as well as the inlet and outlet, tubular pieces 11, 12, practically every usual material for such measurement pickups can be used, such as e.g. alloys of iron, titanium, zirconium and/or tantalum, synthetic materials, or ceramics. For the case where the measurement pickup is to be releasably assembled with the pipeline, first and second flanges 13, 14 are preferably formed on the inlet tube piece 11 and the outlet tube piece 12, respectively; if required, the inlet and outlet tube pieces can, however, also be connected directly to the pipeline, e.g. by means of welding or brazing. Additionally, as shown schematically in FIG. 1, the transducer housing 100 is provided, fixed to the inlet and outlet tube pieces 11, 12, for accommodating the measuring tube 10; compare, in this connection, FIGS. 1 and 2.

At least for measuring the mass flow rate m, the measuring tube 10 is excited in a first useful mode of oscillation developed as a lateral oscillation mode, in which it executes, at least in part, oscillations, especially bending oscillations, laterally to an imaginary measuring tube longitudinal axis L, especially such that it bends laterally outwards, essentially oscillating at a natural bending eigenfrequency, according to a natural, first form of eigenoscillation. For the case where the medium is flowing in the connected pipeline and, consequently, the mass flow rate m is different from zero, the measuring tube 10, oscillating in the first useful mode of oscillation, induces Coriolis forces in the medium as it flows through. These, in turn, interact with the measuring tube 10 and result, in the manner known to those skilled in the art, in an additional, sensor-detectable deformation of the measuring tube 10 essentially according to a natural, second form of eigenoscillation coplanarly superimposed on the first form of eigenoscillation. The instantaneous shape of the deformation of the measuring tube 10 is, in such case, especially as regards its amplitudes, also dependent on the instantaneous mass flow rate m.

As usual in the case of such measurement pickups, anti-symmetric forms of bending oscillation of two, or four, antinodes can e.g. serve as the second form of eigenoscillation, the so-called Coriolis mode. Since natural eigenfrequencies of such modes of lateral oscillation of measuring tubes are known to depend, in special measure, also on the density ρ of the medium, also the density ρ can be measured, without more, by means of the inline measuring device, in addition to the mass flow rate m. In addition to the lateral oscillations, the at least one measuring 10 is also driven, at least at times, in a torsional mode of oscillation, for producing viscosity-dependent, shear forces in the flowing medium. In this torsional mode of oscillation, the measuring tube is excited to torsional oscillations about an axis of torsional oscillation extending essentially parallel to, or coinciding with, the longitudinal axis L of the measuring tube.

Essentially, this excitement is such that the measuring tube 10 is twisted about its longitudinal axis L in a form of natural, torsional oscillation; compare, in this connection, e.g. also U.S. Pat. No. 4,524,610, U.S. Pat. No. 5,253,533, U.S. Pat. No. 6,006,609 or EP-A 1 158 289. The exciting of the torsional oscillations can, in such case, occur either in alternation with the first useful mode of oscillation and separated therefrom, in a second useful mode of oscillation, or, at least in the case of mutually distinguishable oscillation frequencies, also simultaneously with the lateral oscillations in the first useful mode of oscillation. Stated differently, the measurement pickup works, at least at times, in a dual-mode of operation, in which the at least one measuring tube 10 is caused to vibrate alternatingly in at least two oscillation modes essentially independent of one another, namely in the lateral oscillation mode and in the torsional oscillation mode.

According to one embodiment of the invention, for producing the mass flow rate-dependent Coriolis forces in the flowing medium, the measuring tube 10 is excited, at least at times, with a lateral oscillation frequency, which corresponds as exactly as possible to a lowest natural bending eigenfrequency of the measuring tube 10, so that, thus, the laterally oscillating measuring tube 10, without fluid flowing through it, is essentially symmetrically bowed outwards with respect to a middle axis perpendicular to the longitudinal axis L of the measuring tube and, in doing so, exhibits a single oscillation antinode. This lowest bending eigenfrequency can be, for example, in the case of a stainless steel tube serving as the measuring tube 10, of nominal diameter 20 mm, wall thickness about 1.2 mm and length about 350 mm, with the usual appendages, about 850 Hz to 900 Hz.

In a further embodiment of the invention, the measuring tube 10 is excited, especially simultaneously to the lateral oscillations in the useful mode, with a torsional oscillation frequency $f_{excT}$, which corresponds as exactly as possible to a natural torsional eigenfrequency of the measuring tube. A lowest torsional eigenfrequency can, for example, lie in the case of a straight measuring tube about in the range of twice the lowest bending eigenfrequency.

As already mentioned, the oscillations of the measuring tube 11 are damped, on the one hand, by transfer of oscillation energy, especially to the medium. On the other hand, however, oscillation energy can also be withdrawn from the vibrating measuring tube to a considerable degree by the excitation of components mechanically coupled therewith into oscillations, components such as e.g. the transducer housing 100 or the connected pipeline. For the purpose of suppressing or preventing a possible loss of oscillation energy to the environment, a counteroscillator 20 is, therefore, provided in the measurement pickup fixed to the inlet and outlet ends of the measuring tube 10. The counteroscillator 20 is, as shown schematically in FIG. 2, preferably embodied as one piece. If required, the counteroscillator 20 can be composed of multiple parts, as shown e.g. also in U.S. Pat. No. 5,969,265, EP-A 317 340 or WO-A 00/14485, or it can be implemented by means of two separate counteroscillator portions fixed to the inlet and outlet ends of the measuring tube 10; compare FIG. 6. The counteroscillator 20 serves, among other things, to balance the measurement pickup dynamically for at least one, predetermined density value of the medium, for example a density value most frequently to be expected, or also a critical density value, to such an extent that transverse forces and/or bending moments possibly produced in the vibrating measuring tube 10 are largely compensated; compare, in this connection, also U.S. Pat. No. 6,691,583. Moreover, the counteroscillator 20 serves for the above-described case, where the measuring tube 10 is also excited during operation to torsional oscillations, additionally to produce counter torsional moments largely compensating such torsional moments as are produced by the single measuring tube 10 preferably twisting about its longitudinal axis L, thus holding the environment of the measurement pickup, especially, however, the connected pipeline, largely free of dynamic torsional moments. The counteroscillator 20 can, as shown schematically in FIGS. 2 and 3, be embodied in tube shape and can be connected, for example, to the inlet end 11# and the outlet end 12# of the measuring tube 10 in such a manner that it is, as shown in FIG. 3, arranged essentially coaxially with the measuring tube 10. The counteroscillator 20 can be made of practically any of the materials also used for the measuring tube 10, thus, for example, stainless steel, titanium alloys, etc.

The counteroscillator 20, which is, especially in comparison to the measuring tube 10, somewhat less torsionally and/or bendingly elastic, is likewise caused to oscillate during operation and, indeed, with essentially the same frequency as the measuring tube 10, but out of phase therewith, especially with opposite phase. To this end, the counteroscillator 20 is caused to oscillate with at least one of its torsional eigenfrequencies tuned as accurately as possible to those torsional oscillation frequencies, with which the measuring tube is predominantly caused to oscillate during operation. Moreover, the counteroscillator 20 is adjusted also in at least one of its bending eigenfrequencies to at least one bending oscillation frequency with which the measuring tube 10, especially in the useful mode, is caused to oscillate, and the counteroscillator 20 is excited during operation of the measurement pickup also to lateral oscillations, especially bending oscillations, which are developed essentially coplanarly with lateral oscillations of the measuring tube 10, especially the bending oscillations of the useful mode.

In an embodiment of the invention shown schematically in FIG. 3, the counteroscillator 20 has, for this purpose, grooves 201, 202, which make possible an exact adjustment of its torsional eigenfrequencies, especially a sinking of the torsional eigenfrequencies through a sinking of a torsional stiffness of the counteroscillator 20. Although the grooves 201, 202 are shown in FIG. 2 or FIG. 3 essentially uniformly distributed in the direction of the longitudinal axis L, they can, if required, also be arranged, without more, distributed non-uniformly in the direction of the longitudinal axis L. Moreover, the mass distribution of the counteroscillator can, as likewise shown schematically in FIG. 3, also be corrected by means of corresponding mass balancing bodies 101, 102 fixed to the measuring tube 10. These mass balancing bodies 101, 102 can be e.g. metal rings pushed onto the measuring tube 10, or small metal plates fixed thereto.

For producing mechanical oscillations of the measuring tube 10, the measurement pickup additionally includes an exciter arrangement 40, especially an electrodynamic one, coupled to the measuring tube. The exciter arrangement 40 serves for converting an electrical exciter power $P_{exc}$ fed from the measuring device electronics, e.g. having a regulated exciter current $i_{exc}$ and/or a regulated voltage, into an e.g. pulse-shaped, or harmonic, exciter moment $M_{exc}$ and/or an exciter force $F_{exc}$ acting on, and elastically deforming, the measuring tube 10. For achieving a highest possible efficiency and a highest possible signal/noise ratio, the exciter power $P_{exc}$ is tuned as exactly as possible such that predominantly the oscillations of the measuring tube 10 in the useful mode are maintained, and, indeed, as accurately as possible to an instantaneous eigenfrequency of the measuring tube containing the medium flowing therethrough. The exciter force $F_{exc}$, as well as also the exciter moment $M_{exc}$, can, in this case, as is shown schematically in FIG. 4 or FIG. 6, each be developed bidirectionally or, however, also unidirectionally, and can be adjusted in the manner known to those skilled in the art, e.g. by means of a current and/or voltage regulating circuit as regards their amplitude and e.g. by means of a phase locked loop as regards their frequency. The exciter arrangement 40 can include, as usual in the case of such vibratory measurement-pickups, for instance a plunger coil arrangement having a cylindrical exciter coil attached to the counteroscillator 20 or to the inside of the transducer housing 100. In operation, the exciter coil has a corresponding exciter current $i_{exc}$ flowing through it. Additionally included in the exciter arrangement 40 is a permanently magnetic armature extending at least partially into the exciter coil and fixed to the measuring tube 10. Furthermore, the exciter arrangement 40 can also be realized by means of a plurality of plunger coils, or also by means of electromagnets, such as e.g. shown in U.S. Pat. No. 4,524,610 or WO-A 03/095950.

For detecting the oscillations of the measuring tube 10, the measurement pickup additionally includes a sensor arrangement 50, which produces, as a representation of vibrations of the measuring tube 10, a first, especially analog, oscillation measurement signal $s_1$ by means of a first oscillation sensor 51 reacting to such vibrations. The oscillation sensor 51 can be formed by means of a permanently magnetic armature, which is fixed to the measuring tube 10 and interacts with a sensor coil mounted on the counteroscillator 20 or the transducer housing. To serve as the oscillation sensor 51, especially such sensors are suited, which detect a velocity of the deflections of the measuring tube 10 based on the electrodynamic principle. However, also acceleration measuring, electrodynamic or even travel-distance measuring, resistive or optical sensors can be used. Of course, other sensors known to those skilled in the art as suitable for detection of such vibrations can be used. The sensor arrangement 60 includes, additionally, a second oscillation sensor 52, especially one identical to the first oscillation sensor 51. The second sensor 52 provides a second oscillation measurement signal S2 likewise representing vibrations of the measuring tube 10. The two oscillation sensors 51, 52 are in this embodiment so arranged in the measurement pickup 10, separated from one another along the length of the measuring tube 10, especially at equal distances from the halfway point of the measuring tube 10, that the sensor arrangement 50 locally registers both inlet-end and outlet-end vibrations of the measuring tube 10 and converts them into the corresponding oscillation measurement signals $s_1$, $s_2$. The two oscillation measurement signals $s_1$, $s_2$, which usually each exhibit a signal frequency corresponding to an instantaneous oscillation frequency of the measuring tube 10, are, as shown in FIG. 2, fed to the measuring device electronics 50, where they are preprocessed, especially digitized, and then suitably evaluated by means of corresponding components.

According to an embodiment of the invention, the exciter arrangement 40 is, as, in fact, shown in FIGS. 2 and 3, so constructed and arranged in the measurement pickup, that it acts, during operation, simultaneously, especially differentially, on the measuring tube 10 and on the counteroscillator 20. In the case of this further development of the invention, the exciter arrangement 40 is, as, in fact, shown in FIG. 2, advantageously so constructed and so arranged in the measurement pickup, that it acts, during operation, simultaneously, especially differentially, on the measuring tube 10 and on the counteroscillator 20. In the example of an embodiment shown in FIG. 4, the exciter arrangement 40 has, for such purpose, at least one first exciter coil 41a, through which the exciter current, or an exciter current component, flows at least at times during operation. The exciter coil 41a is fixed to a lever 41c connected to the measuring tube 10 and acts differentially on the measuring tube 10 and the counteroscillator 20 via this lever and an armature 41b fixed externally to the counteroscillator 20. This arrangement has, among others, the advantage that, on the one hand, the counteroscillator 20, and thus also the transducer housing 20, is kept small in cross section and, in spite of this, the exciter coil 41a is easily accessible, especially also during assembly. Moreover, a further advantage of this embodiment of the exciter arrangement 40 is that possible used coil cups 41d, which especially at nominal diameters of over 80 mm, have weights which can no longer be ignored, are fixable on the counteroscillator 20 and, consequently, have practically no influence on the eigenfrequencies of the measuring tube 10. It is to be noted here, however, that, in case required, the exciter coil 41a can also be held by the counteroscillator 20 and the armature 41b, then, by the measuring tube 10.

In corresponding manner, the oscillation sensors 51, 52 can be so designed and arranged in the measurement pickup that the vibrations of the measuring tube 10 and the counteroscillator 20 are registered differentially by them. In the example of an embodiment shown in FIG. 5, the sensor arrangement 50 includes a sensor coil 51a fixed to the measuring tube 10, here outside of all principal axes of inertia of the sensor arrangement 50. The sensor coil 51a is arranged as close as possible to an armature 51b fixed to the counteroscillator 20 and magnetically so coupled with such, that a changing measurement voltage is induced in the sensor coil, influenced by rotary and/or lateral, relative movements between measuring tube 10 and counteroscillator 20 in changing their relative position and/or their relative separation. On the basis of such an arrangement of the sensor coil 51*a*, both the above-mentioned torsional oscillations and the excited bending oscillations can, advantageously, be registered simultaneously. If necessary, the sensor coil 51*a* therefor can, however, also be fixed to the counteroscillator 20 and the armature 51*b* coupled therewith can, correspondingly, then be fixed to the measuring tube 10.

In another embodiment of the invention, measuring tube 10, counteroscillator 20 and the sensor and exciter arrangements 40, 50 secured thereto are so matched to one another with respect to their mass distribution, that the resulting inner part of the measurement pickup, suspended by means of the inlet and outlet tube pieces 11, 12, has a center of mass MS lying at least inside of the measuring tube 10, and preferably as close as possible to the longitudinal axis L of the measuring tube. Additionally, the inner part is advantageously so constructed that it has a first principal axis of inertia $T_1$ aligned with the inlet tube piece 11 and the outlet tube piece 12 and lying at least sectionally within the measuring tube 10. Due to the displacement of the center of mass MS of the inner part, especially, however, also due to the above-described position of the first principal axis of inertia $T_1$, the two oscillation forms assumed in operation by the measuring tube 10 and largely compensated by the counteroscillator 20, namely the torsional oscillations and the bending oscillations of the measuring tube 10, are highly mechanically decoupled from one another; compare, in this connection, also WO-A 03/095950. In this way, the two forms of oscillation, thus lateral oscillations and/or torsional oscillations, are advantageously, without more, excited separately from one another. Both the displacement of the center of mass MS and also the first principal axis of inertia $T_1$ toward the longitudinal axis of the measuring tube can, for example, be considerably simplified by having the inner part, thus measuring tube 10, counteroscillator 20 and the sensor and exciter arrangements 50, 40 secured thereto, so constructed and arranged with respect to one another, that a mass distribution of the inner part along the length of the measuring tube longitudinal axis L is essentially symmetrical, at least, however, invariant relative to an imaginary rotation about the longitudinal axis L of the measuring tube by 180° (c2-symmetry). Additionally, the counteroscillator 20—here tubularly, especially also largely axially symmetrically, embodied—is arranged essentially coaxially with the measuring tube 10, whereby the reaching of a symmetrical distribution of mass in the inner part is significantly simplified, and, consequently, also the center of mass MS is displaced in simple manner close to the longitudinal axis L of the measuring tube. Moreover, the sensor and exciter arrangements 50, 40 in the example of an embodiment presented here are so constructed and arranged relative to one another on the measuring tube 10 and, where appropriate, on the counteroscillator 20, that a mass moment of inertia produced by them is developed as concentrically as possible to the longitudinal axis L of the measuring tube or at least is kept as small as possible. This can e.g. be achieved by having a common center of mass of sensor and exciter arrangements 50, 40 lie as close as possible to the longitudinal axis L of the measuring tube and/or by keeping the total mass of sensor and exciter arrangements 50, 40 as small as possible.

In a further embodiment of the invention, the exciter arrangement 40 is, for the purpose of the separated exciting of torsional and/or bending oscillations of the measuring tube 10, so constructed and so fixed to the measuring tube 10 and to the counteroscillator 20, that a force producing the bending oscillations acts on the measuring tube 10 in the direction of an imaginary line of force extending outside of a second principal axis of inertia $T_2$ perpendicular to the first principal axis of inertia $T_1$, or intersecting the second principal axis of inertia in, at most, one point. Preferably, the inner part is so embodied that the second principal axis of inertia $T_2$ is essentially the above-mentioned middle axis. In the example of an embodiment shown in FIG. 4, the exciter arrangement 40 has, for this purpose, at least one first exciter coil 41*a*, through which the exciter current or an exciter current component flows at least at times during operation. Exciter coil 41*a* is fixed to a lever 41*c* connected with the measuring tube 10 and via this lever and an armature 41*b* fixed externally to the counteroscillator 20, acts differentially on the measuring tube 10 and the counteroscillator 20. This arrangement has, among other things, also the advantage that, on the one hand, the counteroscillator 20 and, consequently, also the transducer housing 100 are kept small in cross section and, in spite of this, the exciter coil 41*a* is easily accessible, especially also during assembly. Moreover, a further advantage of this embodiment of the exciter arrangement 40 is that possibly used coil cups 41*d*, which especially at nominal diameters of over 80 mm have weights that no longer can be neglected, can likewise be fixed to the counteroscillator 20 and, consequently, have practically no effect on the resonance frequencies of the measuring tube. It should be noted here that, when required, the exciter coil 41*a* can also be mounted to the counteroscillator 20 and then the armature 41*b* is held by the measuring tube 10.

According to a further embodiment of the invention, the exciter arrangement 40 has at least one, second exciter coil 42*a* arranged along a diameter of the measuring tube 10 and coupled with the measuring tube 10 and the counteroscillator 20 in the same way as the exciter coil 41*a*. According to another, preferred embodiment of the invention, the exciter arrangement has two further exciter coils 43*a*, 44*a*, thus a total of four, at least arranged symmetrically with respect to the second principal axis of inertia $T_2$. All coils are mounted in the measurement pickup in the above-described manner. The force acting on the measuring tube 10 outside of the second principal axis of inertia $T_2$ can be produced by means of such two, or four, coil arrangements in simple manner e.g. by having one of the exciter coils, e.g. the exciter coil 41*a*, exhibit another inductance than the respective others, or by causing to flow through one of the exciter coils, e.g. the exciter coil 41*a*, during operation, an exciter current component that is different from a respective exciter current component of the respectively other exciter coils.

Figure 5:
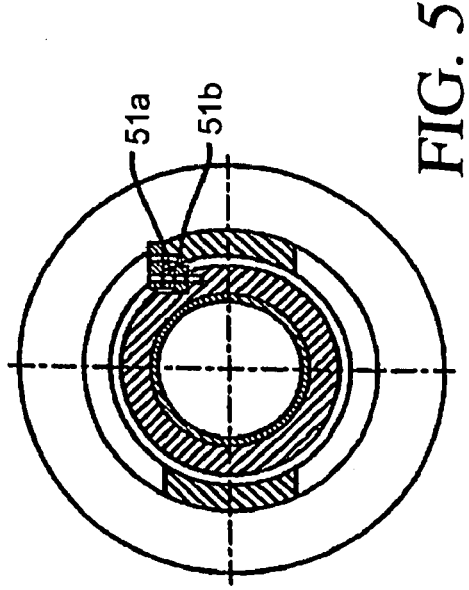
FIG. 5 shows the measurement pickup of FIG. 2 in a second cross section.

According to another embodiment of the invention, the sensor arrangement 50 includes, as shown schematically in FIG. 5, a sensor coil 51*a* arranged outside of the second principal axis of inertia $T_2$ and fixed to measuring tube 10. The sensor coil 51*a* is arranged as near as possible to an armature 51*b* fixed to the counteroscillator 20 and is magnetically coupled therewith such that a changing measurement voltage is induced in the sensor coil, influenced by rotary and/or lateral relative movements between measuring tube 10 and counteroscillator 20 as they change their relative positions and/or their relative separations. Due to the arrangement of the sensor coil 51*a* according to the invention, both the above-described torsional oscillations and the bending oscillations, excited where appropriate, can be registered in advantageous manner simultaneously. If required, the sensor coil 51*a* therefor can, instead, be fixed to the counteroscillator 20 and, in corresponding manner, the armature 51*b* coupled therewith can be fixed to the measuring tube 10.

It is noted here, additionally, that the exciter arrangement 40 and the sensor arrangement 50 can also have, in the manner known to those skilled in the art, essentially the same mechanical structure; consequently, the above-described embodiments of the mechanical structure of the exciter arrangement 40 can essentially also be transferred to the mechanical structure of the sensor arrangement 50, and vice versa.

For vibrating the measuring tube 10, the exciter arrangement 40 is, as already mentioned, fed with a likewise oscillating exciter current $i_{exc}$, especially a multifrequency current, of adjustable amplitude and adjustable exciter frequency $f_{exc}$ such that this current flows through the exciter coils 26, 36 during operation and the magnetic fields required for moving the armatures 27, 37 are produced in corresponding manner. The exciter current $i_{exc}$ can be e.g. harmonically multifrequent or even rectangular. The lateral oscillation exciter frequency $f_{excL}$ of a lateral current component $i_{excL}$ of the exciter current $i_{exc}$ required for maintaining the lateral oscillations of the measuring tube 10 can advantageously be so chosen and adjusted in the case of the measurement pickup shown in the example of an embodiment that the laterally oscillating measuring tube 10 oscillates essentially in a bending oscillation base mode having a single oscillation antinode. Analogously thereto, also a torsional oscillation frequency $f_{excT}$ of a torsional current component $i_{excT}$ of the exciter current $i_{exc}$ required for maintaining the torsional oscillations of the measuring tube 10 can advantageously be so chosen and adjusted in the case of the measurement pickup shown in the example of an embodiment that the torsionally oscillating measuring tube 10 oscillates essentially in a torsional oscillation base mode having a single oscillation antinode. The two mentioned current components $i_{excL}$ and $i_{excT}$ can, depending on the type of operation selected, be fed into the exciter arrangement 40 intermittently, thus instantaneously each acting as the exciter current $i_{exc}$, or also simultaneously, thus supplementing one another to form the effective exciter current $i_{exc}$.

For the above-described case wherein the lateral oscillation frequency $f_{excL}$ and the torsional oscillation frequency $f_{excT}$, with which the measuring the measuring tube 10 is caused to oscillate during operation, are adjusted differently from one another, a separation of the individual oscillation modes can occur both in the exciter signals and also in the sensor signals, by means of the measurement pickup in simple and advantageous manner, even in the case of simultaneously excited torsional and bending oscillations, e.g. based on a signal filtering or a frequency analysis. Otherwise, an alternating exciting of the lateral and torsional oscillations recommends itself.

For producing and adjusting the exciter current $i_{exc}$, or the current components $i_{excL}$, $i_{excT}$, the measuring device electronics includes a corresponding driver circuit 53, which is controlled by a lateral oscillation frequency adjustment signal $y_{FML}$ representing the desired lateral oscillation exciter frequency $f_{excL}$ and by a lateral oscillation amplitude adjustment signal $y_{AML}$ representing the desired lateral oscillation amplitude of the exciter current $i_{exc}$ and/or the lateral current component $i_{excL}$, as well as, at least at times, by a torsional oscillation frequency adjustment signal $y_{FMT}$ representing the torsional oscillation exciter frequency $f_{excT}$ and by a torsional oscillation amplitude adjustment signal $y_{AMT}$ representing the desired torsional oscillation amplitude of the exciter current $i_{exc}$ and/or the torsional current component $i_{excT}$. The driver circuit 53 can be realized e.g. by means of a voltage-controlled oscillator or a downstream voltage-to-current converter; instead of an analog oscillator, however, also a numerically controlled, digital oscillator can be used to set the instantaneous exciter current $i_{exc}$ or the components $i_{excL}$, $i_{excT}$ of the exciter current.

An amplitude control circuit 51 integrated into the measuring device electronics 50 can serve for producing the lateral amplitude adjustment signal $y_{AML}$ and/or the torsional oscillation amplitude adjustment signal $y_{AMT}$. The amplitude control circuit 51 actualizes the amplitude adjustment signals $y_{AML}$, $y_{AMT}$ on the basis of instantaneous amplitudes of at least one of the two oscillation measurement signals $s_1$, $s_2$ measured at the instantaneous lateral oscillation frequency and/or the instantaneous torsional oscillation frequency, as well as on the basis of corresponding, constant or variable amplitude reference values for the lateral and torsional oscillations, respectively $W_B$, $W_T$; as appropriate, also instantaneous amplitudes of the exciter current $i_{exc}$ can be referenced for generating the lateral oscillation amplitude adjustment signal $y_{AML}$ and/or the torsional oscillation amplitude adjustment signal $y_{AMT}$; compare FIG. 7. Construction and manner of operation of such amplitude control circuits are likewise known to those skilled in the art. As an example for such an amplitude control circuit, reference is made, moreover, to the measurement transmitters of the series "PROMASS 80", such as are available from the assignee, for example in connection with measurement pickups of the series "PROMASS I". Their amplitude control circuit is preferably so constructed that the lateral oscillations of the measuring tube 10 are controlled to a constant amplitude, thus an amplitude also independent of the density $\rho$.

The frequency control circuit 52 and the driver circuit 53 can be constructed e.g. as phase-locked loops, which are used in the manner known to those skilled in the art for adjusting the lateral oscillation frequency adjusting signal $y_{FML}$ and/or the torsional oscillation frequency adjusting signal $y_{FMT}$ continuously for the instantaneous eigenfrequencies of the measuring tube 10 on the basis of a phase difference measured between at least one of the oscillation measurement signals $s_1$, $s_2$ and the exciter current $i_{exc}$ to be adjusted, respectively the instantaneously measured exciter current $i_{exc}$. The construction and use of such phase-locked loops for the driving of measuring tubes at one of their mechanical eigenfrequencies is described in detail in e.g. U.S. Pat. No. 4,801,897. Of course, other frequency control circuits known to those skilled in the art can be used, such as are proposed in U.S. Pat. No. 4,524,610 or U.S. Pat. No. 4,801,897. Furthermore, reference is made to the already mentioned measurement transmitters of the series "PROMASS 80" respecting a use of such frequency control circuits for vibratory measurement pickups. Other circuits suitable for use as driver circuits can be learned from, for example, U.S. Pat. No. 5,869,770 or U.S. Pat. No. 6,505,519.

According to a further embodiment of the invention, the amplitude control circuit 51 and the frequency control circuit 52 are, as shown schematically in FIG. 7, realized by means of a digital signal processor DSP provided in the measuring device electronics 50 and by means of program code correspondingly implemented in such and running therein. The program codes can be stored persistently or even permanently e.g. in a non-volatile memory EEPROM of a microcomputer 55 controlling and/or monitoring the signal processor and loaded upon startup of the signal processor DSP into a volatile data memory RAM of the measuring device electronics 50, e.g. RAM integrated in the signal processor DSP. Signal processors suited for such applications are e.g. those of type TMS320VC33 available from the firm Texas Instruments Inc. It is clear, in this regard, that the oscillation measurement signals $s_1$, $s_2$ need to be converted by means of corresponding analog-to-digital converters A/D into corresponding digital signals for a processing in the signal processor DSP; compare, in this connection, especially EP-A 866,319. In case required, adjustment signals output from the signal processor, such as e.g. the amplitude adjusting signals $y_{AML}$, $y_{AMT}$, or the frequency adjusting signals $y_{FML}$, $y_{FMT}$, can be, in corresponding manner, converted from digital to analog.

As shown in FIG. 7, the, if appropriate, first suitably conditioned, oscillation measurement signals $s_1$, $s_2$ are additionally sent to a measurement circuit 21 of the measuring device electronics for producing the at least one measured value $X_X$ on the basis of at least one of the oscillation measurement signals $s_1$, $s_2$ and/or on the basis of the exciter current $i_{exc}$.

According to an embodiment of the invention, the measurement circuit 21 is constructed, at least in part, as a flow rate calculator and the measurement circuit serves for determining, in the manner known per se to those skilled in the art, from a phase difference detected between the oscillation measurement signals $s_1$, $s_2$ generated in the case of a measuring tube 10 oscillating laterally at least in part, a measured value $X_X$ serving here as a mass flow rate measured value and representing, as accurately as possible, the mass flow rate to be measured. The measurement circuit 21 can be any, especially digital, measuring circuit already used in conventional Coriolis mass flow measuring devices for determining the mass flow rate on the basis of the oscillation measurement signals $s_1$, $s_2$; compare, in this connection, especially the initially mentioned WO-A 02/37063, WO-A 99/39164, U.S. Pat. No. 5,648,616, U.S. Pat. No. 5,069,074. Of course, other measuring circuits known to those skilled in the art to be suitable for Coriolis mass flow measuring devices can be used, i.e. measuring circuits which measure, and correspondingly evaluate, phase and/or time differences between oscillation measurement signals of the described kind.

Additionally, the measurement circuit 21 can also serve to utilize an oscillation frequency of the at least one measuring tube 11, as measured, for example, on the basis of at least one of the oscillation measurement signals $s_1$, $s_2$, for generating a measured value $X_X$ usable as a density measured value instantaneously representing a density $\rho$ to be measured for the medium or a phase of the medium.

Because the straight measuring tube 10 is, as above described, caused to execute, during operation, lateral and torsional oscillations simultaneously or alternatingly, the measurement circuit can also be used to determine (derived from the exciter current $i_{exc}$, which, it is known, can serve also as a measure for an apparent viscosity or also a viscosity-density product) a measured value $X_X$ usable as a viscosity measured value and instantaneously representing a viscosity of the medium; compare, in this connection, also U.S. Pat. No. 4,524,610 or WO-A 95 16 897.

It is clear in this connection, without more, for those skilled in the art, that the inline measuring device can determine the separate measured values $X_x$ for the various measured quantities x both in a common measuring cycle, thus with equal updating rates, as well as with different updating rates. For example, a very accurate measurement of the usually significantly varying mass flow rate requires usually a very high updating rate, while the comparatively less variable viscosity of the medium can, where appropriate, be updated at larger separations in time. Additionally, it can, without more, be assumed that currently determined, measured values $X_x$ can be stored temporarily in the measuring device electronics and, therefore, be available for subsequent uses. Advantageously, the measurement circuit 21 can, furthermore, also be implemented by means of the signal processor DSP.

As already mentioned at the start, inhomogeneities and/or the formation of first and second phases in the flowing medium, for example gas bubbles and/or solid particles entrained in liquids, can lead to the result that a measured value determined in conventional manner assuming a single-phase and/or homogeneous medium will not match with sufficient accuracy the actual value of the quantity x whose measurement is desired, for example the mass flow rate m, i.e. the measured value must be appropriately corrected. This preliminarily determined, provisionally representing, or at least corresponding, value of the physical quantity x whose measurement is desired, which value, as already explained, can, for example, be a phase difference $\Delta\phi$ measured between the oscillation measurement signals $s_1$, $s_2$, or a measured oscillation frequency, of the measuring tube 11, is, consequently, referenced in the following as an initial measured value, or also a beginning measured value, $X'_x$. From this initial measured value $X'_x$, the evaluation electronics 21, in turn, finally derives the measured value $X_x$ representing the physical, measured quantity x sufficiently accurately, whether the physical, measured quantity x is the mass flow rate, the density, or the viscosity. Considering the very comprehensive and very well documented and detailed state of the art, it can be assumed that the determination of the initial measured value $X'_x$, which, for practical purposes, corresponds to the measured value generated in conventional manner, presents no difficulties for those skilled in the art, so that the initial measured value $X'_x$ can be taken as a given for the further explanation of the invention.

There is already discussion in the state of the art with reference to the mentioned inhomogeneities in the medium that these can immediately show up both in the phase difference measured between the two oscillation signals $s_1$, $s_2$ and in the oscillation amplitude or the oscillation frequency of each of the two oscillation measurement signals, respectively exciter current, thus in practically all of the usually measured, directly or indirectly, operational parameters of measuring devices of the described kind. This is true, especially in the case of the operational parameters determined with a laterally oscillating measuring tube, as is treated in WO-A 03/076880 or U.S. Pat. No. 6,505,519; it can, however, also not always be excluded for operational parameters measured with a torsionally oscillating measuring tube—compare, in this connection, especially U.S. Pat. No. 4,524,610.

Further investigations by the inventors have, however, led to the surprising discovery that, while it is true, the instantaneous exciter current $i_{exc}$ and, going along therewith, a damping of the oscillations of the measuring tube 10 usually likewise measured in the operation of the measuring device, do depend to a significant amount on the degree of the inhomogeneity of the two, or more, phase medium and/or on a concentration of a second medium phase thereof, for example, thus on a characteristic, a distribution and/or an amount of gas bubbles and/or solid particles entrained in a liquid being measured, nevertheless, both for lateral and for torsional oscillations—at least in the two base modes mentioned above—a largely reproducible and, consequently, at least experimentally determinable relationship can be postulated between the particular current component $i_{excL}$, $i_{excT}$ instantaneously required for maintaining the lateral, respectively torsional, oscillation and the instantaneous degree of inhomogeneity of the two, or more, phase medium, or even the instantaneous concentration of a second phase of the medium, especially a second phase acting as a disturbance.

Surprisingly, it has additionally been found that, in spite of the fact that both an instantaneous damping of the lateral oscillations and, as is discussed especially in U.S. Pat. No. 4,524,610 or EP-A 1 291 639, an instantaneous damping of the torsional oscillations are dependent significantly on the degree of the inhomogeneity or on the concentrations of individual phases of the medium, simultaneous, or at least contemporaneous, determination of the instantaneous dampings of both of the oscillation modes permits an amazingly robust and very reproducible correction of the intermediate value $X'_x$ and, therefore, the generating of a very accurate measured value $X_x$. Further investigations have shown, namely, that the damping both of the lateral oscillations and the torsional oscillations is, indeed, very strongly dependent on the viscosity of the medium to be measured. At the same time, the damping of the lateral oscillations shows a very strong dependence on the degree of inhomogeneities of the medium instantaneously present in the measuring tube 10, while, in contrast, the dependence of the damping of the torsional oscillations on inhomogeneities in the medium is far weaker.

According to the invention, for the purpose of improving the accuracy with which the physical, measured quantity x, for example the mass flow rate m or the density ρ, is determined, the measurement pickup is operated, at least at times, in the previously mentioned dual-mode, in which the at least one measuring tube 10—in turns and/or alternatingly—is caused to vibrate in the lateral oscillation mode and/or in the torsional oscillation mode. For the correction of the first determined, initial, measured value $X'_x$ sought accordingly, the measuring device electronics 2 determines, during operation, an, especially digital, first intermediate value $X_1$, which essentially corresponds to the damping of the lateral oscillation mode, and an, especially digital, second intermediate value $X_2$, which essentially corresponds to the medium-dependent damping of the torsional oscillation mode. The determining of the first intermediate value proceeds here essentially based on the lateral current component $i_{excL}$ of the exciter current $i_{exc}$, especially the regulated component, required for maintaining the lateral oscillations, while, for determining the second intermediate value $X_2$, especially the torsional current component $i_{excT}$, especially the regulated component, required for maintaining the torsional oscillations is taken into consideration. Using the two intermediate values $X_1$, $X_2$, the measurement circuit 21 additionally determines an, especially likewise digital, correction value $X_K$ for the intermediate value $X'_x$. The correction of the intermediate value $X'_x$ on the basis of the correction value $X_K$, as well as the generating of the measured value $X_x$, can occur in the measuring device electronics, for example, based on the mathematical relationship $$X_x = K_x \cdot (1 + X_K) \cdot X'_x. \qquad (1)$$

In an embodiment of the invention, the correction value $X_K$ is determined by means of the measuring device electronics based on the mathematical relationship $$X_K = K_K \cdot (X_1 - X_2), \qquad (2)$$

so that this essentially represents a measure of the deviation ΔD of damping measured during operation for the principally excited, lateral and torsional oscillations. Alternatively, or for supplementing such, the correction value $X_K$ can also be determined based on the mathematical relationship $$X_K = K'_K \cdot \left(1 - \frac{X_2}{X_1}\right). \qquad (3)$$

While, thus, in Eq. (2), the correction value $X_K$ is determined on the basis of a difference ΔD existing between the intermediate value $X_1$ and the intermediate value $X_2$, in the case of Eq. (3), the correction value $X_K$ is determined on the basis of a comparison of the second intermediate value $X_2$ with the first intermediate value $X_1$. In this respect, the correction value $X_K$ represents, at least for a two-phase medium, also a measure for an instantaneous, relative or absolute, concentration of a first and a second phase of a medium, especially for gas bubbles in a liquid. Besides the generating of the actual measured value $X_x$, the correction value $X_K$ can, therefore, also be converted into a concentration measured value $X_C$, which represents, in the case of a two, or more, phase medium in a measuring tube, an, especially relative, volume and or mass fraction of a phase of a medium. Furthermore, the correction value $X_K$ can also be used to signalize the degree of inhomogeneity of the medium, or measured values derived therefrom, such as e.g. a percentage air content in the medium or a volume, quantity or mass fraction of solid particles entrained in the medium, e.g. on site or visually perceivable in a remote control room. Alternatively or additionally, the correction value $X_K$ can also serve for signalizing for the user, for example out of a comparison with an initially defined limit value, that, for the instantaneous flow conditions in the measuring tube 10, the measured quantity x is being measured with considerable uncertainty and/or with a large amount of error. Additionally, the correction value $X_K$ can, in this case, also be used to switch off a signal output which issues the measured value $X_x$ for the measured quantity x of interest during operation.

Figure 9:
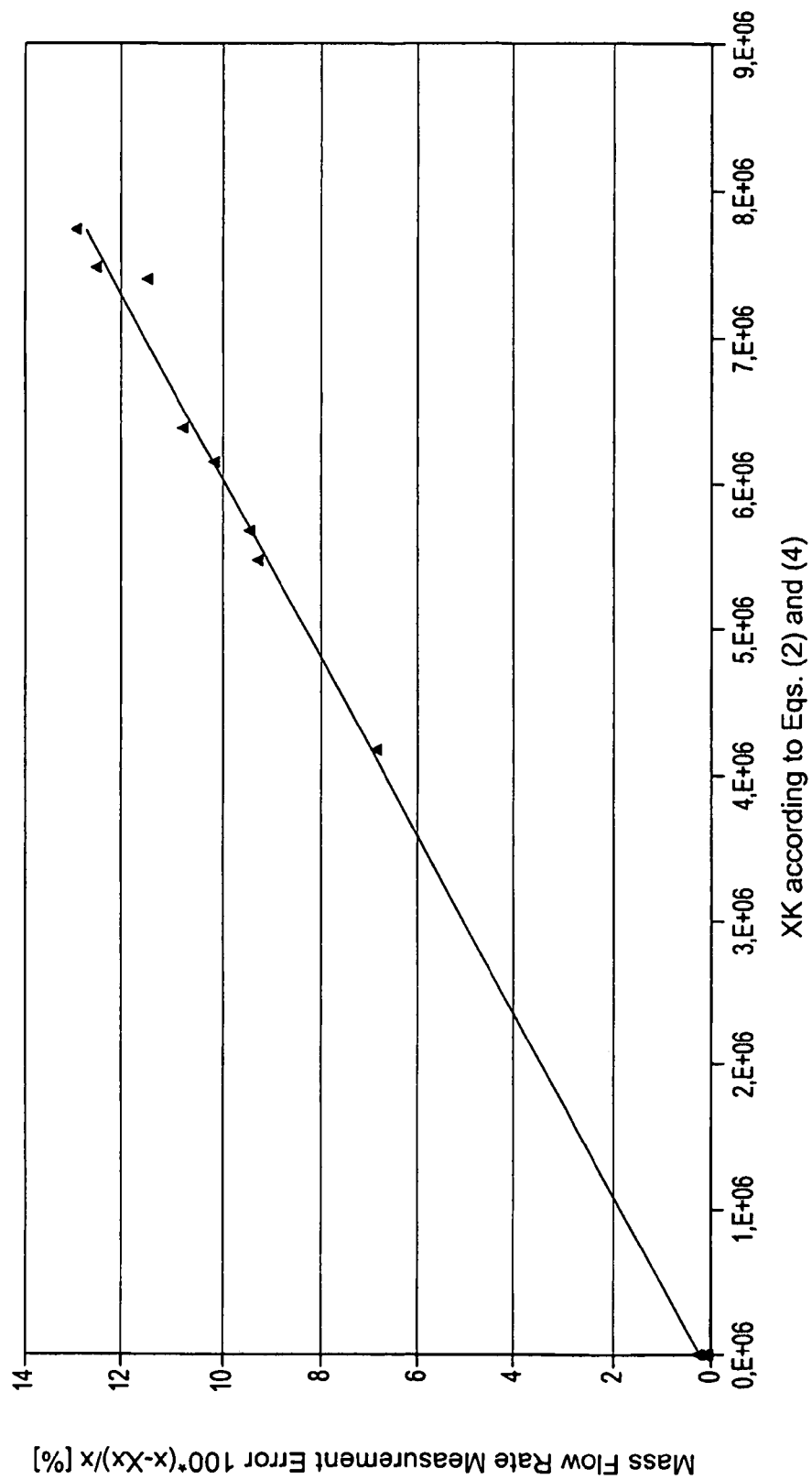

Further experimental investigations have shown that, for a measurement pickup of the illustrated example of an embodiment, the consideration of the instantaneous lateral oscillation frequency of the vibrating measuring tube can lead to a further improvement of the accuracy of the measured value $X_x$. Moreover, by a normalizing of the correction value $X_K$ determined on the basis of Eq. (2) or Eq. (3) on the square root of the instantaneous lateral oscillation frequency, one finds that the correction value $X_K$ is essentially proportional to the gas fraction, at least for the case wherein a liquid, for example glycerin, contains entrained gas bubbles, for example air; compare, in this connection, also FIG. 9. Therefore, in a further development of the invention, Eq. (2) is modified using a lateral oscillation frequency measured value $X_{fexcL}$ representing the instantaneous lateral oscillation frequency, as follows:

$$X_K = K_K \cdot \frac{(X_1 - X_2)}{\sqrt{X_{fexcL}}}. \qquad (4)$$

The determining of the lateral oscillation frequency measured value can transpire simply e.g. on the basis of the above-mentioned lateral oscillation frequency adjusting signal $y_{FML}$.

In the determining of the two intermediate values $X_1$, $X_2$, it is additionally to be kept in mind that the damping of the oscillations of the measuring tube 10 is determined both by the damping component attributable to viscous frictions within the medium and by a damping component which is practically independent of the medium. This latter damping component is caused by mechanical friction forces, which act e.g. in the exciter arrangement 40 and in the material of the measuring tube 10. Stated differently, the instantaneously measured exciter current $i_{exc}$ represents the totality of the frictional forces and/or frictional moments in the measurement pickup 10, including the mechanical frictions in the measurement pickup and the viscous friction in the medium. In determining the intermediate values $X_1$, $X_2$, which, as mentioned, mainly are related to the damping components of the oscillations of the measuring tube resulting from viscous frictions in the medium, the mechanical damping components, which are independent of the medium, must be appropriately considered, for example they should be separated out or eliminated.

For determining the intermediate value $X_1$, therefore, an embodiment of the invention provides that, from an, especially digital, lateral current measured value $X_{iexcL}$ instantaneously representing the lateral current component $i_{excL}$, a correspondingly associated, lateral, empty-state, electrical current, measured value $K_{iexcL}$ is subtracted, which represents the mechanical friction forces in each case arising in the instantaneously excited, lateral oscillation mode in the measurement pickup in the case of empty measuring tube 10. In the same manner, for determining the intermediate value $X_2$, from an, especially digital, torsional current measured value $X_{iexcT}$ instantaneously representing the torsional current component $i_{excT}$, a torsional, empty-state, electrical current, measured value $K_{iexcT}$ is subtracted, which represents the mechanical frictional forces in each case arising in the instantaneously excited, torsional oscillation mode in the measurement pickup in the case of empty measuring tube 10.

Figure 8:
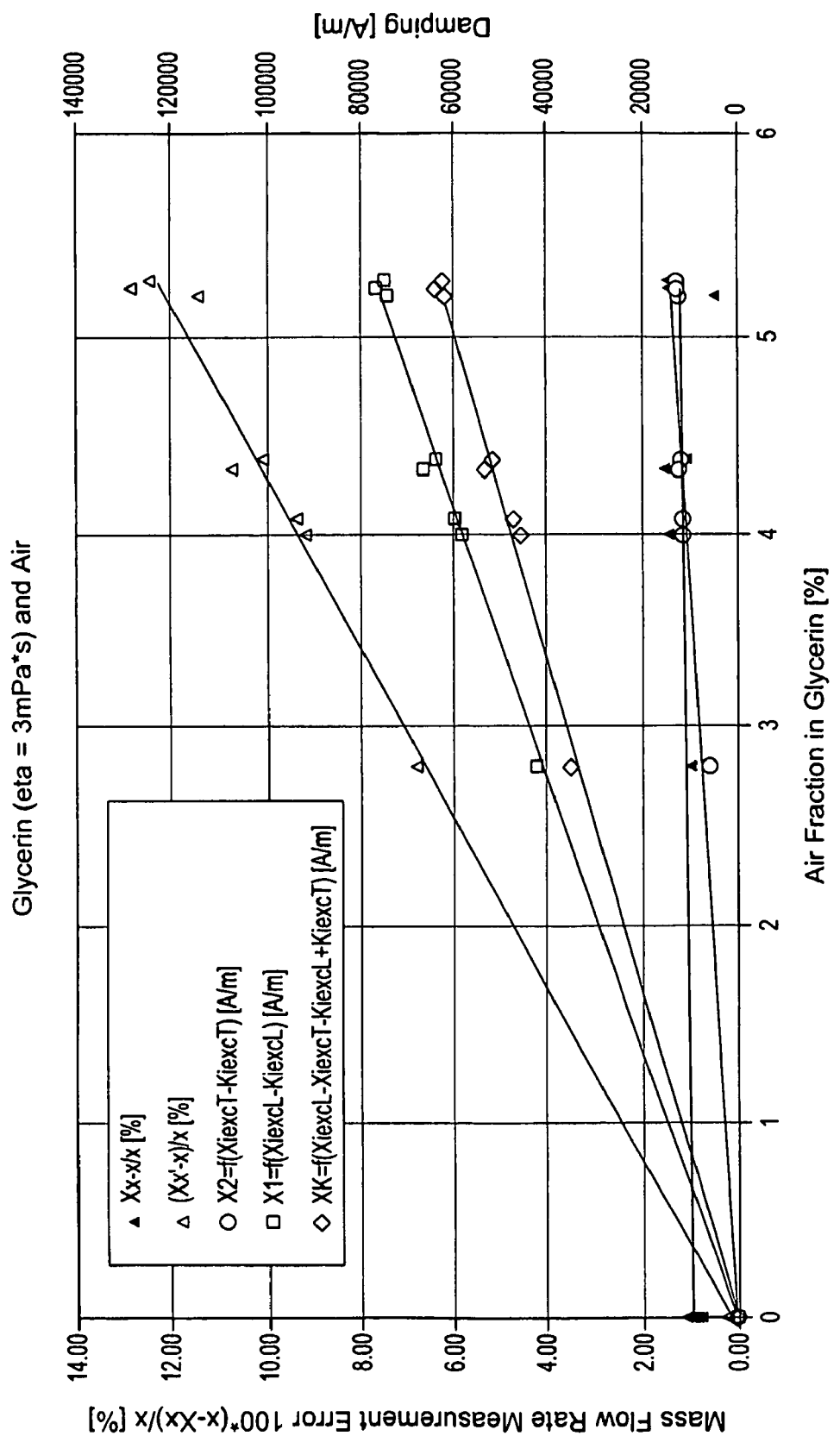

According to a further embodiment of the invention, the determining of the intermediate value $X_1$ occurs, as also shown in FIG. 8 by way of example on electrical current, measured values $X_{iexcL}$, $X_{iexcT}$ and empty-state, electrical current, measured values $K_{iexcL}$, $K_{iexcT}$ experimentally determined for the correction of the mass flow rate on the basis of the lateral current component $i_{excL}$ driving the lateral oscillations and on the basis of the associated lateral, empty-state, electrical current, measured value $K_{iexcL}$, especially based on the mathematical relationship $$X_1 = K_1 \cdot (X_{iexcL} - K_{iexcL}) \tag{5}$$

and/or based on the mathematical relationship $$X_1 = K_1' \cdot \left(1 - \frac{K_{iexcL}}{X_{iexcL}}\right). \tag{6}$$

In case required, especially in the case of significantly varying, vibratory measuring tube, oscillation amplitudes and/or vibratory measuring tube, oscillation amplitudes deviating from the calibrated reference values, the lateral current component $i_{excL}$ can initially likewise be normalized on the instantaneous oscillation amplitude of the lateral oscillations of the measuring tube, for example using the oscillation measurement signals $s_1$, $s_2$.

Analogously thereto, also the intermediate value $X_2$ can be determined based on the mathematical relationship $$X_2 = K_2 \cdot (X_{iexcT} - K_{iexcT}) \tag{7}$$

and/or based on the mathematical relationship $$X_2 = K_2' \cdot \left(1 - \frac{K_{iexcT}}{X_{iexcT}}\right). \tag{8}$$

Each of the empty-state, electrical current, measured values $K_{iexcL}$, $K_{iexcT}$, as also the device-specific coefficients $K_k$, $K_k'$, $K_1$, $K_2$, $K_1'$ or $K_2'$ is likewise to be determined during a calibration of the inline measuring device, e.g. using an evacuated or air-carrying measuring tube, and stored, or set, appropriately in the measuring device electronics 50, especially normalized on the oscillation amplitude measured at such time. It is clear, without more, for those skilled in the art, that, if necessary, other physical parameters influencing the empty-state, electrical current, measured values $K_{iexcL}$, $K_{iexcT}$, such as e.g. an instantaneous temperature of the measuring tube and/or of the medium, are to be taken into consideration during the calibration.

For calibrating the measured values pickup 10, usually two, or more, different, two, or more, phase, media with varying, but known, flow parameters, such as e.g. known concentrations of the individual medium phases of the calibrating medium, whose density ρ, mass flow rate m, viscosity η and/or temperature are known, are caused to flow in turn through the measurement pickup 10, and the corresponding reactions of the measured values pickup 10, such as e.g. the instantaneous exciter current $i_{exc}$, the instantaneous lateral oscillation exciter frequency $f_{excL}$ and/or the instantaneous torsional oscillation exciter frequency $f_{excT}$ are measured. The adjusted flow parameters and the respectively measured reactions of the measured operational parameters of the measurement pickup 10 are related to one another in appropriate manner and, thus, mapped onto the corresponding calibration constants. For example, for determining the constants during the calibration measurements for two calibration media of known viscosity held as constant as possible and of different inhomogeneity, which, however, in each case, is formed in a manner which remains constant, a ratio $X_x'/x$ and/or $X_x/x$ of the intermediate value $X_x'$ determined in each case, respectively, of the measured value $X_x$ determined in each case, to the then, in each case, current, actual value of the quantity being measured is formed for known air fraction. For example, the first calibration medium can be flowing water, or even oil, with entrained air bubbles, and the second calibration medium can be water which is as homogeneous as possible. The calibration constants determined here can then be stored e.g. in the form of digital data in a table memory of the measuring device electronics; they can, however, also serve as analog adjustment values for corresponding computing circuits. It is to be noted here that the calibration of measurement pickups of the described type is a subject known per se, or at least executable from the above explanations, for those skilled in the art, and, consequently does not require any further explanation. Advantageously, the already mentioned lateral oscillation amplitude adjustment signal $y_{AML}$ and/or the torsional oscillation amplitude adjustment signal $y_{AMT}$ can be used for determining the lateral current, measured value $X_{iexcL}$ and/or the torsional current, measured value $X_{iexcT}$, since these represent the exciter current $i_{exc}$, or its components $i_{excL}$, $i_{excT}$ sufficiently accurately for the correction.

According to a further embodiment of the invention, for the already multiply-mentioned case where the measured quantity x to be registered corresponds to a viscosity, or even a fluidity, and so the measured value $X_x$ serves as a viscosity measured-value, also the initial measured-value $X_x'$ is determined on the basis of the exciter current $i_{exc}$ driving the exciter arrangement 40 in the case of a measuring tube at least partially torsionally oscillating, especially on the basis of the torsional current component $i_{excT}$ serving for maintaining the torsional oscillations of the measuring tube 10. Taking into consideration the relationship already described in U.S. Pat. No. 4,524,610:

$$\sqrt{\eta} \sim i_{excT}, \quad (9)$$

according to which the torsional current component $i_{excT}$, reduced by the above-mentioned, torsional, empty-state, electrical current, measured value $K_{iexcT}$, correlates very well with the square root of the actual viscosity, $\eta$, at least in the case of constant density, $\rho$, and largely homogeneous medium, in corresponding manner first a squared value $X_{\Delta iexcT}^2$ of the torsional current, measured value $X_{iexcT}$ is formed inside the measuring device electronics, reduced by the torsional, empty-state, electrical current, measured value $K_{iexcT}$ and derived from the exciter current $i_{exc}$, for the determining of the initial measured value $X_x'$. Considering that, as, in fact, also explained in U.S. Pat. No. 4,524,610, the square of the current does, in fact, provide the information on the product of density and viscosity, the actual density, which, for example, can be determined initially, likewise by means of the inline measuring device, is, moreover, to be taken into consideration when determining the initial measured value $X_x'$ in the aforedescribed manner.

In a further embodiment of the invention, for forming the initial measured value $X_\eta$, the square $X_{iexcT}^2$ of the torsional current, measured value $X_{iexcT}$ is, moreover, by means of a simple, numerical division, normalized on an amplitude measured value $X_{sT}$, which represents instantaneously, in the case of a torsionally oscillating measuring tube, an operationally determined, in certain cases varying, signal amplitude of at least one of the oscillation measurement signals $s_1$, $s_2$. It has, namely, also been found, that, for such viscosity measuring devices having such a vibratory measurement pickup, especially also in the case of constantly controlled oscillation amplitude and/or in the case of simultaneous exciting of lateral and torsional oscillations, a ratio $i_{exc}/\theta$ of the exciter current $i_{exc}$ to a practically not directly measurable velocity $\theta$ of a movement causing the internal frictions and, thus, also the frictional forces in the medium, is a more accurate estimate of the already mentioned damping acting against the excursions of the measuring tube 10. Consequently, for further increasing the accuracy of the measured value $X_x$, especially, however, also for decreasing its sensitivity to fluctuating oscillation amplitudes of the vibrating measuring tube 10 possibly arising during operation, it is further provided that, for the determining of the initial measured value $X_x'$, the torsional current measured value $X_{iexcT}$ is first normalized on the amplitude measured value $X_{sT}$, which represents the above-mentioned velocity $\theta$ sufficiently accurately. Stated differently, a normalized torsional current measured value $X'_{iexcT}$ is formed according to the following formula:

$$X'_{iexcT} = \frac{X_{iexcT}}{X_{sT}}. \quad (10)$$

The amplitude measured value $X_{s1}$ is, based on the recognition that the movement causing the viscous friction in the medium matches very strongly the movement of the vibrating measuring tube 10 registered locally by means of the sensor 51 or also by means of the sensor 52, preferably derived using the measuring device electronics 50, e.g. by the internal amplitude measurement circuit, from at least one, possibly already digitized, sensor signal $s_1$. It is noted here, again, that the sensor signal $s_1$ is preferably proportional to a velocity of an, especially lateral, excursion of the vibrating measuring tube 10; the sensor signal $s_1$ can, however, also be proportional to an acceleration acting on the vibrating measuring tube or to a distance covered by the vibrating measuring tube 10. For the case, where the sensor signal $s_1$ is designed to be velocity-proportional in the above sense, this is, of course, to be considered in the determining of the initial measured value.

The aforementioned functions serving for the production of the measured value $X_x$, symbolized by the Eqs. (1) to (10), can be implemented, at least in part, by means of the signal processor DSP or e.g. also by means of the above-mentioned microcomputer 55. The creation and implementation of corresponding algorithms matching such equations or mimicking the functioning of the amplitude control circuit 51, respectively the frequency control circuit 52, and their transformation into program code executable in such signal processors, is, per se, within the skill of the art, and, consequently, does not require any detailed explanation, particularly once the present disclosure has been reviewed. Of course, these equations can also, without more, be represented by means of corresponding, discretely assembled, analog and/or digital, simulating circuits in the measuring device electronics 50.

In a further development of the invention, the correction value $X_K$ instantaneously appropriate during operation is determined, starting from the intermediate values $X_1$, $X_2$, practically directly by representing in the measuring device electronics, especially in a program, a unique relationship between a present combination of the two intermediate values $X_1$, $X_2$ and the correction value $X_K$ belonging therewith. To this end, the measuring device electronics 2 additionally has a table memory, in which a set of predetermined, digital correction values $X_{K,i}$ is stored, for example values determined during the calibration of the Coriolis mass flow measuring device. These correction values $X_{K,i}$ are accessed directly by the measurement circuit via a memory address determined by means of the instantaneously valid intermediate values $X_1$, $X_2$. The correction value $X_K$ can be determined e.g. in simple manner by comparing a combination of the instantaneously determined intermediate values $X_1$, $X_2$, for example the above-mentioned damping difference, with corresponding prestored values stored for this combination in the table memory and, on the basis of this comparison, that correction value $X_{K,i}$ is read out, thus used by the evaluation electronics 2 for the further calculations, which corresponds to the prestored value having the closest match with the instantaneous combination. The table memory can be a programmable, fixed-value memory, thus a FPGA (field programmable gate array), an EPROM or an EEPROM. The use of such a table memory has, among others, the advantage that the correction value $X_K$ is available during runtime very quickly following calculation of the intermediate values $X_1$, $X_2$. Moreover, the correction values $X_{K,i}$ entered in the table memory can be predetermined very accurately, e.g. based on the Eqs. (2), (3) and/or (4) and making use of the method of least squares.

As can be appreciated, without more, from the above presentation, a correction of the initial measured value $X'_x$ can be carried out, on the one hand, using few correction factors which are very easy to determine. Also, the correction can be performed using the two intermediate values $X_1$, $X_2$ with a computing effort, which is quite small in comparison to the more complexly developed computing methods known from the state of the art. An additional advantage of the invention is to be seen in the fact that at least some of the described correction factors can be generated, without more, from the flow parameters determined, for example, by means of conventional Coriolis mass flow measuring devices, especially the measured density and/or the—here provisionally—measured mass flow rate, and/or from the operational parameters usually directly measured in the operation of Coriolis mass flow measuring devices, especially the measured oscillation amplitudes, oscillation frequencies and/or derived from the exciter current, and, consequently without noticeable increase of the circuit and measurement complexity.

The invention claimed is:

1. An inline measuring device, especially a Coriolis mass-flow/density measuring device and/or a viscosity measuring device, for the measurement of at least one physical, measured quantity x, especially a mass flow rate, m, a density, $\rho$, and/or a viscosity, $\eta$, of a medium, especially a two, or more, phase medium, guided in a pipeline, which inline measuring device comprises:
   a vibratory-type measurement pickup; and
   measuring device electronics electrically coupled with said vibratory-type measurement pickup, wherein said measurement pickup includes:
   at least one measuring tube, especially an essentially straight measuring tube, inserted into the course of the pipeline, serving to guide the medium to be measured, and communicating with the connected pipeline;
   an exciter arrangement acting on said at least one measuring tube for causing said at least one measuring tube to vibrate, which, during operation, causes the measuring tube to vibrate at least at times and/or at least partially with lateral oscillations, especially bending oscillations, and which, during operation, causes the measuring tube to vibrate at least at times and/or at least partially with torsional oscillations, especially with torsional oscillations alternating with the lateral oscillations or at times superimposed thereon, about an imaginary measuring tube longitudinal axis essentially aligned with said at least one measuring tube, especially such an axis in the form of a principal axis of inertia of the measuring tube; and
   a sensor arrangement for registering vibrations of said at least one measuring tube and for delivering at least one oscillation measurement signal ($s_1$, $s_2$) representing oscillations of said measuring tube, further wherein:
   said measuring device electronics delivers, at least at times, an exciter current ($i_{exc}$) driving the exciter arrangement,
   said measuring device electronics further determines a first intermediate value ($X_1$), which corresponds to a lateral current component ($i_{excL}$) of the exciter current ($i_{exc}$) serving to maintain the lateral oscillations of the measuring tube and/or a damping of the lateral oscillations of the measuring tube, and a second intermediate value ($X_2$), which corresponds to a torsional current component ($i_{excT}$) of the exciter current ($i_{exc}$) serving to maintain the torsional oscillations of the measuring tube and/or a damping of the torsional oscillations of the measuring tube; and
   said measuring device electronics by means of at least one oscillation measurement signal ($s_1$, $s_2$) and/or by means of the exciter current ($i_{exc}$), and using the first and the second intermediate values ($X_1$, $X_2$), generates, at least at times, at least one measured value ($X_x$), which represents at least one physical quantity to be measured, especially the mass flow rate, m, the density, $\rho$, or the viscosity, $\eta$, of the medium.

2. The iline measuring device as claimed in claim 1, wherein:
   said measuring device electronics determines a initial measured value ($X'_x$) derived from the at least one oscillation measurement signal ($s_1$, $s_2$) and/or from the exciter current ($i_{exc}$), the initial measured value ($X'_x$) corresponds, at least approximately, with the at least one quantity to be measured, and the measuring device electronics (2) further determines, on the basis of the first and the second intermediate values ($X_1$, $X_2$) a correction value ($X_K$) for the initial measured value ($X'_x$), and
   said measuring device electronics generates the measured value ($X_x$) by means of the initial measured value ($X'_x$) and the correction value ($X_K$).

3. The inline measuring device as claimed in claim 1, wherein:
   said at least one measuring tube, driven by said exciter arrangement, executes torsional oscillations with a measuring tube torsional oscillation frequency set to be different from a measuring tube bending oscillation frequency with which said at least one measuring tube, driven by said exciter arrangement, executes lateral oscillations.

4. The inline measuring device as claimed in claim 1, wherein:
   said at least one measuring tube communicates with the connected pipeline via an inlet tube piece opening into an inlet end and via an outlet tube piece opening into an outlet end; and
   said measurement pickup includes a counteroscillator fixed to said inlet end and to said outlet end, especially a counteroscillator also mechanically coupled with said exciter arrangement, and the counteroscillator vibrates during operation at least at times, especially with phase opposite to that of said at least one measuring tube.

5. The inline measuring device as claimed in claim 1, wherein:
   said measuring device electronics determines the correction value ($X_K$) on the basis of a comparison of the first intermediate value ($X_1$) with the second intermediate value ($X_2$) and/or on the basis of a difference existing between the first intermediate value ($X_1$) and the second intermediate value ($X_2$).

6. The inline measuring device as claimed in claim 1, wherein:
   said measuring device electronics produces the first and/or the second intermediate value ($X_1$, $X_2$) using the at least one oscillation measurement signal ($s_1$, $s_2$).

7. The inline measuring device as claimed in claim 1, wherein;
   the at least one measured value ($X_x$) represents a viscosity, $\eta$, of the medium flowing in said at least one measuring tube; and
   said measuring device electronics also determines the initial measured value ($X'_x$) by means of the exciter current ($i_{exc}$) driving said exciter arrangement and/or by means of a component of the exciter current ($i_{excL}$, $i_{excT}$).

8. The inline measuring device as claimed in claim 1, wherein:
   the at least one measured value ($X_x$) represents a density, $\rho$, of the medium flowing in said at least one measuring tube; and
   said measuring device electronics determines the initial measured value ($X'_x$) using the at least one oscillation measurement signal ($s_1$, $s_2$) and/or the exciter current ($i_{exc}$) in a manner such that the initial measured value corresponds to the density, ρ, to be measured, and/or to an oscillation frequency of the at least one oscillation measurement signal ($s_1$, $s_2$).

9. The inline measuring device as claimed in claim 1, wherein:

said measuring device electronics determines, at least at times, on the basis of the first and the second intermediate values ($X_1$, $X_2$) a concentration measured value ($X_C$), which represents, in the case of a two, or more, phase medium in said at least one measuring tube, an, especially relative, volume and/or mass fraction of a phase of the medium.

10. The inline measuring device as claimed in claim 1, wherein:

said sensor arrangement delivers at least one first oscillation measurement signal ($s_1$), which represents, at least in part, inlet-end lateral oscillations, especially bending oscillations, of said at least one measuring tube, and at least one second oscillation measurement signal ($s_2$), which represents, at least in part, outlet-end lateral oscillations, especially bending oscillations, of said at least one measuring tube.

11. The inline measuring device as claimed in claim 1, wherein:

the at least one measured value ($X_x$) represents a mass flow rate, m, of the medium flowing in said at least one measuring tube; and said measuring device electronics determines the initial measured value ($X'_x$) using the two oscillation measurement signals ($s_1$, $s_2$) in a manner such that the initial measured value corresponds to the mass flow rate, m, to be measured and/or to a phase difference, Δφ, between the two oscillation measurement signals ($s_1$, $s_2$).

12. The use of an inline measuring device as claimed in claim 1 for measuring a physical, measured quantity, especially a mass flow rate, a density and/or a viscosity, of a two, or more, phase medium, especially a liquid-gas mixture, flowing in a pipeline.

13. A method for measuring a physical, measured quantity, especially mass flow rate, a density and/or a viscosity, of a medium flowing in a pipeline, especially a two, or more, phase medium, by means of an inline measuring device having a vibration-type measurement pickup, especially a Coriolis mass flow measuring device, and measuring device electronics electrically coupled with the measurement pickup, which method comprises the following steps:

allowing the medium to be measured to flow through at least one measuring tube of the measurement pickup, with the measuring tube being in communication with the pipeline; feeding an exciter current ($i_{exc}$) into an exciter arrangement mechanically coupled with the measuring tube guiding the medium, for causing the measuring tube to execute mechanical oscillations;

causing the measuring tube to execute lateral oscillations, especially bending oscillations, and causing the measuring tube to execute torsional oscillations, especially torsional oscillations superimposed on the lateral oscillations;

registering vibrations of the measuring tube and producing at least one oscillation measurement signal ($s_1$, $s_2$) representing oscillations of the measuring tube;

determining a first intermediate value ($X_1$) derived from the exciter current ($i_{exc}$), which corresponds to a lateral current component ($i_{excL}$) of the exciter current ($i_{exc}$) serving to maintain the lateral oscillations of the measuring tube and/or to a damping of the lateral oscillations of the measuring tube;

determining a second intermediate value ($X_2$), derived from the exciter current ($i_{exc}$) which corresponds to a torsional current component ($i_{excT}$) of the exciter current serving to maintain the torsional oscillations of the measuring tube and/or to a damping of the torsional oscillations of the measuring tube; and using the at least one oscillation measurement signal ($s_1$, $s_2$) and/or the exciter current ($i_{exc}$), together with the first and second intermediate values ($X_1$, $X_2$), for producing a measured value ($X_x$) representing the physical, measured quantity, x, to be measured.

14. The method as claimed in claim 13, wherein:

the step of producing the measured value ($X_x$) comprises the following further steps: developing a initial measured value ($X'_x$) corresponding, at least approximately, with the physical quantity to be measured, using the at least one oscillation measurement signal ($s_1$, $s_2$) and/or the exciter current ($i_{exc}$); producing a correction value ($X_K$) for the initial value ($X'_x$) by means of the first and second intermediate values ($X_1$, $X_2$); and correcting the initial measured value ($X'_x$) by means of the correction value ($X_K$) for producing the measured value ($X_x$).

15. The method as claimed in claim 13, wherein:

the step of producing the correction value ($X_K$) for the initial measured value ($X'_x$) comprises the following further steps: comparing the first intermediate value ($X_1$) with the second intermediate value ($X_2$) for determining a difference existing between the two intermediate values ($X_1$, $X_2$), and determining a concentration measured value ($X_C$), which in the case of a two, or more, phase medium in the measuring tube represents a volume and/or mass fraction of a phase of the medium, especially a relative fraction, taking into consideration the difference existing between the two intermediate values ($X_1$, $X_2$).

* * * * *